US008252768B2

(12) United States Patent
Greer

(10) Patent No.: US 8,252,768 B2
(45) Date of Patent: Aug. 28, 2012

(54) DESIGNER THERAPY OF PANCREATIC TUMORS

(75) Inventor: Sheldon B. Greer, Miami, FL (US)

(73) Assignee: University of Miami, Miami, FL (US)

( * ) Notice: Subject to any disclaimer, the term of this patent is extended or adjusted under 35 U.S.C. 154(b) by 162 days.

(21) Appl. No.: 12/472,910

(22) Filed: May 27, 2009

(65) Prior Publication Data

US 2009/0325897 A1     Dec. 31, 2009

Related U.S. Application Data

(63) Continuation-in-part of application No. PCT/US2007/085613, filed on Nov. 27, 2007.

(60) Provisional application No. 60/861,088, filed on Nov. 27, 2006.

(51) Int. Cl.
*A01N 43/04* (2006.01)
*A61K 31/70* (2006.01)
(52) U.S. Cl. ............... 514/49; 514/43; 514/52
(58) Field of Classification Search .................. None
See application file for complete search history.

(56) References Cited

U.S. PATENT DOCUMENTS 5,026,835 A     6/1991 Ueda et al.
5,985,266 A *   11/1999 Link et al. ............... 424/93.21
6,933,287 B1*   8/2005 Greer ............... 514/49

OTHER PUBLICATIONS

Wempen et al. JACS (1961), vol. 83, pp. 4755-4766.*
Mekras et al. Cancer Research (1984), vol. 44, pp. 2551-2560.*
Eidinoff et al. Cancer Research (1959), vol. 19, pp. 638-642.*
Brust et al. Cancer Gene Therapy (2000), vol. 7, pp. 778-788.*
Wingo et al., "New Report Show first Sustained Decline in U.S. Cancer Rates" J. Reg. Management, 25:43-51 (1998).
Mekras J., Boothman D. and Greer, "Use of 5-Trifluoromethyldeoxycytidine and Tetrahydrouridine to Circumvent Catabolism and Exploit High Levels of Cytidine Deaminase in Tumors to Achieve DNA- and Target-Directed Therapies" S. Cancer Res. 45:5270-5280, 1985.
Fingl et al., in The Pharmacological Basis of Therapeutics, 1975, Ch. 1 p. 1-45.
Perez and Greer, "Sensitization to X-Ray by 5-Chloro-2'-Deoxyctidine Co-Administered with Tetrahydrouridine in Several Mammalian Cell Lines and Studies of 2'-Chloro Derivatives" (Int. J. Rad. Oncology: Biology, Physics 12, 1523-1527, 1986.
Greer, S., et al. I"Five-Chlorodeoxycytidine, A Tumor-Selective Enzyme-Driven Radiosensitizer, Effectively controls Five advance Human Tumors in Nude Mice" Int J. Rad. Oncol. Biol. Phys. 51: 791-806 (2001).

Greer, S., et al. "Pyrimidine Metabolizlng Enzyme-Driven Cancer Chemotherapy, Radiation therapy and Selective Rescue" Miami Nature Biotechnology Winter Symposium 14:55 (2003).
Fox, L., Dobersen, M.J., and Greer, S. Incorporation of 5-Substituted Analogs of Deoxycytidine into DNA of Herpes Simplex Virus-Infected or -Transformed Cells Without Deamination to the Thymidine Analog. Antimicrobial Agents and Chemotherapy 23:465-476 (1983).
Cooper, G.M. Phosphorylation of 5-Bromodeoxycytidine in cells infected with Herpes Simplex Virus Proc Natl. Acad. Sci. 70: 3788-3792 (1973).
Greer, S., Schildkraut, I., Zimmerman, T., and Kaufman, H. "5-Halogenated Analogs of Deoxycytidine as Selective Inhibitors of the Replication of Herpes Simplex Viruses in Cell Culture and Related Studies of Intracranial Herpes Simplex Virus infections in Mice" Annals of the N.Y. Acad. of Sci.: Chemistry, Biology and Clinical Uses of Nucleoside Analogs 255:359-365 (1975).
Cooper, G.M., and Greer, S. "Phosphorylation of 5-Halogenated Deoxycytidine analogues by Deoxycytidine Kinase" Mol. Pharm. 9:704-710 (1973).
Cooper, G.M. and Greer, S. "The Effect of Inhibition of Cytidine Deaminase by Tetrahydrouridine on the Utilization of Deoxyctidine and 5-Bromodeoxycytidine for Deoxyribonucleic Acid Synthesis" Mol. Pharm. 9:698-703 (1973).
Fan, J., et al. "Halogenated Thymidine Analogues Restore the Expression of Silenced Genes with out Demethylation" Cancer Res. 65: 6927-6933 (2005).
Barletta, J. and Greer, S. "Methylation of HSV-1 DNA as a mechanism of viral inhibition:studies of an analogue of methyldeoxycytidine: trifluormethyldeoxycytidine (F3mdCyd)" Antiviral Research 18:1-25 (1992).
Spector R. and Huntoon S. "Deoxycytidine Transport and Metabolism in the Central Nervous System" J. Neurochem. 41:1131-1136 (1983).
Schildkraut, et al. "Selective Inhibition of the Replication of Herpes simplex Virus by 5-Halogenated Analogues of Deoxycytidine" Molecular Pharmacology, 11: p. 153-158. (1975).
"Remington's Pharmaceutical Sciences" 15th Edition, chapter 33, pp. 624-652 (1975).

* cited by examiner

*Primary Examiner* — Patrick Lewis
(74) *Attorney, Agent, or Firm* — Novak Druce + Quigg LLP

(57) ABSTRACT

Chemotherapeutic and Radiation sensitizing agents which target tumor cells, specifically, based on the elevation of enzyme pathways, provide highly selective drug therapy. These agents are combined with modulating doses of cytidine deaminase inhibitors to increase selectivity. Furthermore, high doses of these cytidine deaminase inhibitors have the potential of counteracting the aggressive and metastatic characteristics of pancreatic tumors. For tumors with high levels of cytidine deaminase, such as pancreatic tumors, this elevation provides a therapeutic approach with prodrugs that require deamination for their activation. For tumors with high levels of uridine/cytidine kinase, a different class of pyrimidine analogs can be activated selectively in tumors for a therapeutic advantage.

21 Claims, 16 Drawing Sheets

Figure 1

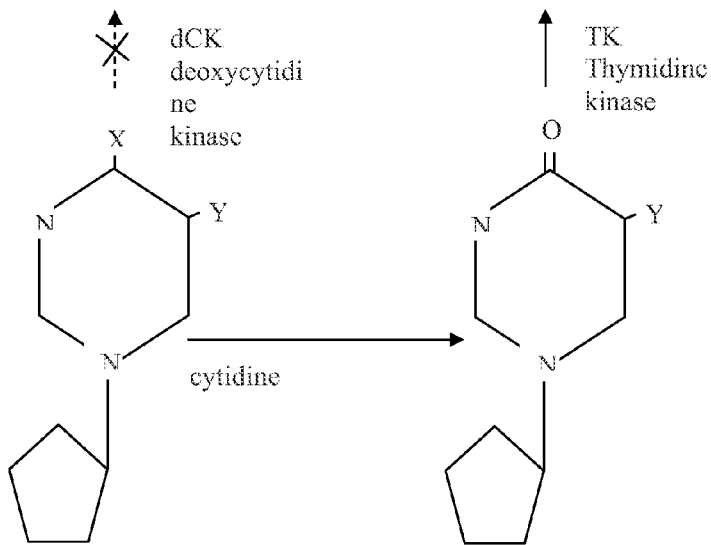

Median CD activity for normal tissue: pancreas, 1.2; breast, 2.9; brain 5.8; rectum, 12. Pancreatic tumors, 20.

IA. The drugs in Category IA are Radiosensitizers
a) 4-N, Methylamino-5-chloro-2'-deoxycytidine (custom synthesized)
X= H-N-CH3   Y=Cl
b) 5-Iodo-2-deoxycytidine
X= H-N-H         Y=I
c) 5-Bromo-2-deoxycytidine
X=H-N-H         Y=Br IB. The drugs in Category IB are Chemotherapeutic Agents
a) 4-N, Methylamino-5-Fluoro-2'-deoxycytidine
X= H-N-CH3   Y=F
b) 5-Trifluoromethyl-2'-deoxycytidine (custom synthesized)
X=H-N-H          Y=CF3
This drug was shown in studies to be superior to 5-FUra, 5-FdU and 5-F3dT vs a mouse tumor (8)

All these drugs will be administered with low loses of Tetrahydrouridine to prevent premature systemic deamination by the liver.

II. Category II drugs are Inhibitors of Cytidine Deaminase. (A collaboration with Dr. Victor Marquez (Medicinal Chemist at the NIH) Tetrahydrouridine, F-Pyrimidine-2one nucleoside, Diazepin-2-1nucleoside; diazoepinone; 2'-fluoro-2'deoxyarabinosyl-tetrahydrouracil

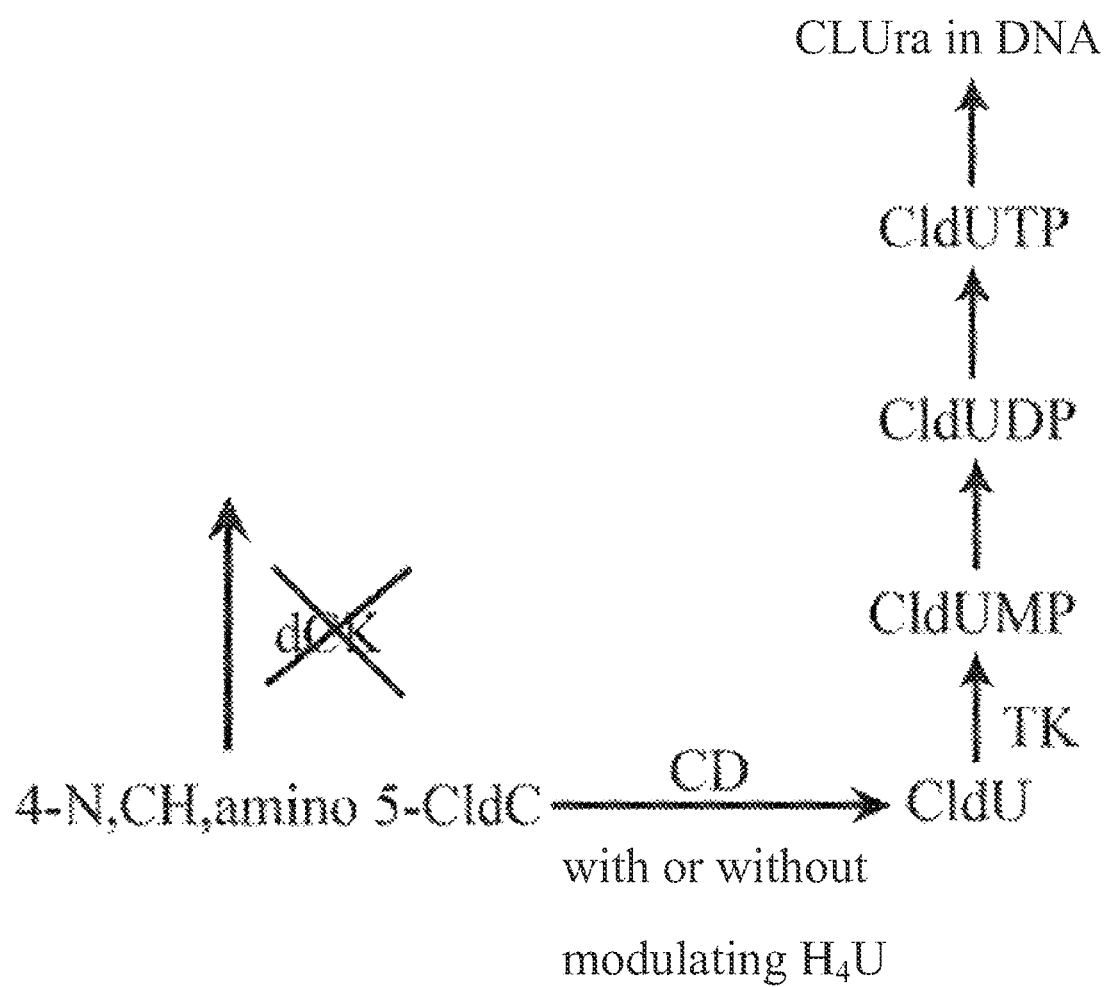

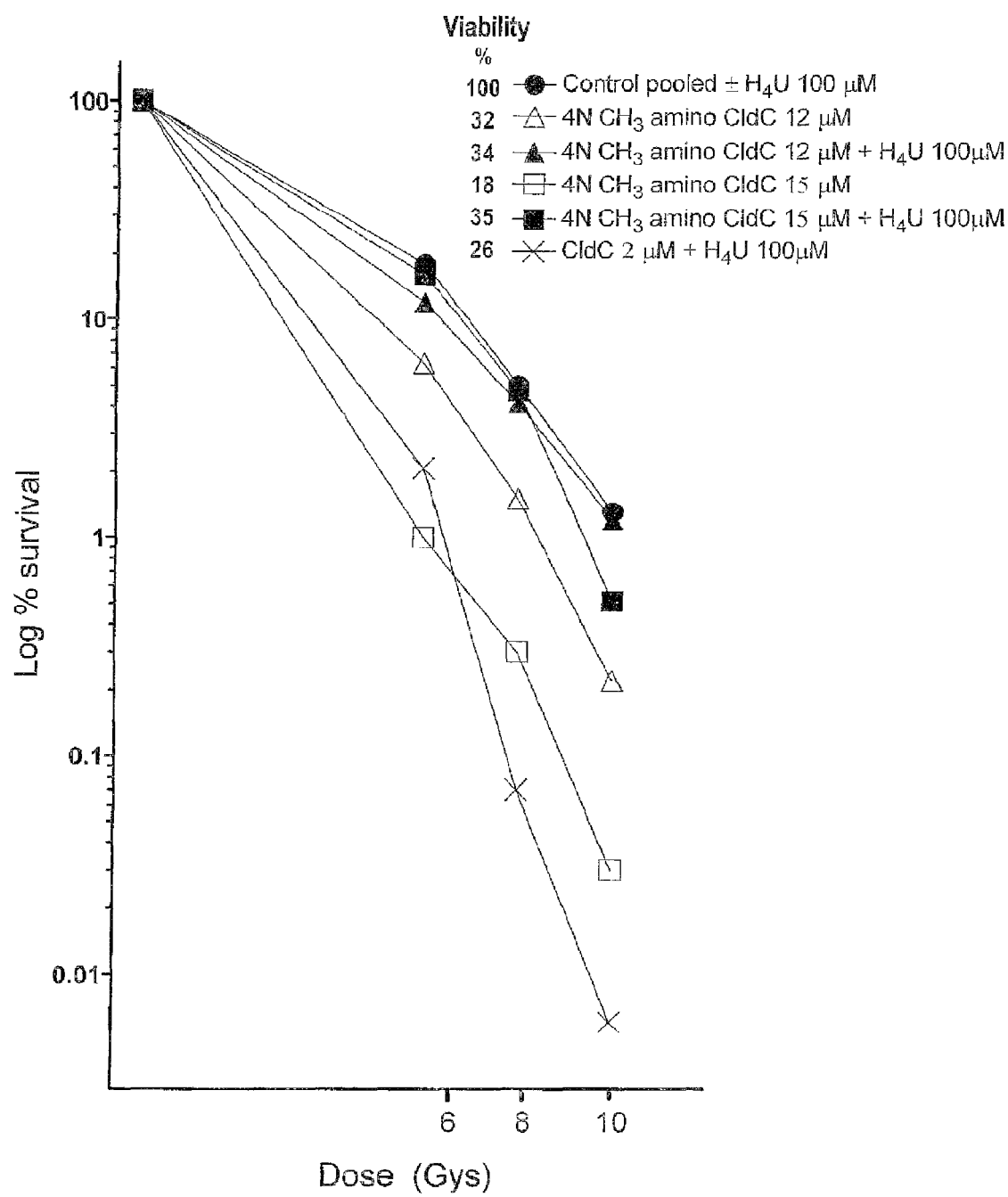

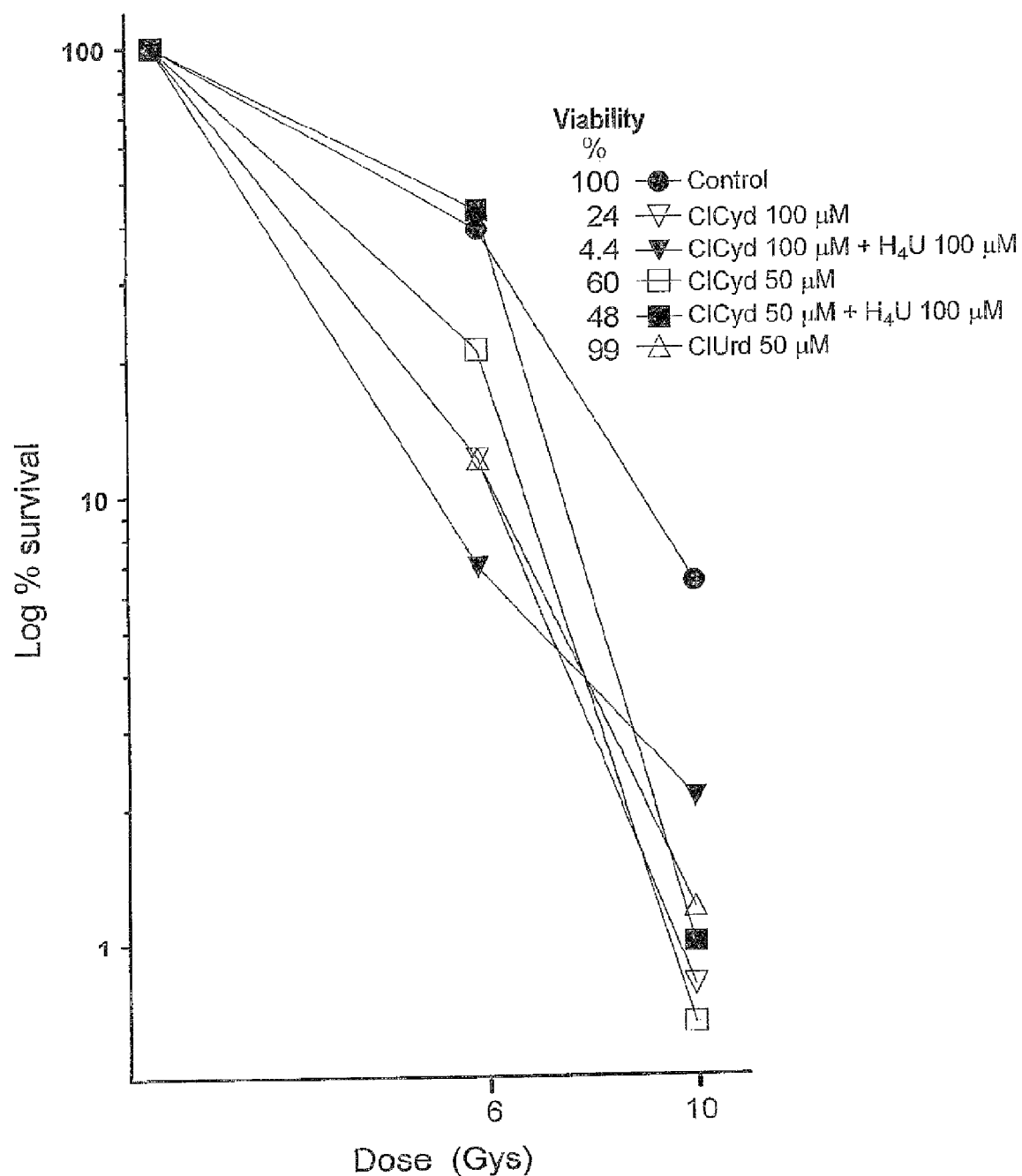

DESIGNER THERAPY OF PANCREATIC TUMORS

CROSS REFERENCE TO RELATED APPLICATIONS

The present application is a Continuation-in-part of International Patent Application Serial No. PCT/US20071085613, filed on Nov. 27, 2007, which claims the benefit of U.S. Provisional Patent Application Ser. No. 60/861,088, filed on Nov. 27, 2006, both of which are hereby incorporated by reference in their entireties.

FIELD OF THE INVENTION

The invention relates to the use of radiosensitizing and chemotherapeutic agents which are incorporated into tumor cell DNA and/or can target thymidylate synthetase via the cytidine deaminase pathway. Combining the agents with cytidine deaminase inhibitors increases the selectivity for tumor cells and decreases any toxicity.

BACKGROUND

Cancer is presently the second leading cause of death in developed nations. Wingo et al. *J. Reg. Management,* 25:43-51 (1998). Despite recent research that has revealed many of the molecular mechanisms of tumorigenesis, few new treatments have achieved widespread clinical success in treating solid tumors. Current treatments for most malignancies thus remain gross resection, chemotherapy, and radiotherapy. While increasingly successful, each of these treatments still causes numerous undesired side effects. The primary cause of these side effects is that none of these conventional methods specifically targets only diseased cells. For example, surgery results in pain, traumatic injury to healthy tissue, and scarring. Radiotherapy and chemotherapy cause nausea, immune suppression, gastric ulceration and secondary tumorigenesis. Furthermore, some types of cancer mean certain death for the patient.

The challenge has been: how can we make a great impact in controlling a disease that is widely known as the most devastating uncontrollable disease that is so certain to kill the patient within three months in so many cases that have been encountered. Pancreatic cancer is known as the "Kiss of Death" and a certain progression to disaster for the patient, the patient's family and friends.

There is thus a need in the art for drugs and therapies which not only selectively target tumor cells, treat previously untreatable tumors and maintain low toxicity when administered to patients.

SUMMARY

Chemotherapeutic and Radiation sensitizing agents which target tumor cells, specifically, based on the elevation of enzyme pathways, provide highly selective drug therapy. These agents are combined with modulating doses of cytidine deaminase inhibitors to increase selectivity. Furthermore, high doses of these cytidine deaminase inhibitors have the potential of counteracting the aggressive and metastatic characteristics of pancreatic tumors. For tumors with high levels of cytidine deaminase, such as pancreatic tumors, this elevation provides a therapeutic approach with prodrugs that require deamination for their activation. For tumors with high levels of uridine/cytidine kinase, a different class of pyrimidine analogs can be activated selectively in tumors for a therapeutic advantage.

In a preferred embodiment, a method of treating a tumor cell comprises administering a radiosensitizing or chemotherapeutic agent, in a therapeutically effective concentration, comprising: a) 4-N, methylamino-5-chloro-2'-deoxycytidine with or without a modulating dose of a cytidine deaminase inhibitor combined with or without one or more sources of radiation; b) 5-Iodo-2'-deoxycytidine with a modulating dose of a cytidine deaminase inhibitor combined with or without one or more sources of radiation; c) 5-Bromo-2'-deoxycytidine with or without a modulating dose of a cytidine deaminase inhibitor combined with or without one or more sources of radiation; d) 5-Trifluoromethyl-2'-deoxycytidine with or without a modulating dose of a cytidine deaminase inhibitor; e) 4-N, methylamino 5-fluoro-2'-deoxycytidine with or without a modulating dose of cytidine deaminase inhibitor; and, treating a tumor cell.

In another preferred embodiment, the tumor is characterized by elevated levels of cytidine deaminase as compared to levels of cytidine deaminase in a normal cell.

In another preferred embodiment, the composition comprises 4-N, methylamino-5-chloro-2'-deoxycytidine in a pharmaceutically acceptable carrier.

In another preferred embodiment, the composition comprises 5-Iodo-2'-deoxycytidine in a pharmaceutically acceptable carrier.

In another preferred embodiment, the composition comprises 5-Bromo-2'-deoxycytidine in a pharmaceutically acceptable carrier.

In another preferred embodiment, the composition comprises 5-Trifluoromethyl-2'-deoxycytidine in a pharmaceutically acceptable carrier.

In another preferred embodiment, the composition comprises 4-N, methylamino FdC in a pharmaceutically acceptable carrier.

In yet another preferred embodiment, the sources of radiation comprise X-rays, γ-rays, protons, brachytherapy, yttrium-90, β-rays, π-mesons, monoclonal antibodies attached to Radionuclides, stereotactic radio surgery, 3-Dimensional Conformal Radiation and Intensity Modified Radiation Therapy.

In another preferred embodiment, the cytidine deaminase inhibitor comprises tetrahydrouridine, or tetrahydro-2'-deoxyuridine.

In another preferred embodiment, the composition is administered to a tumor cell in an amount effective to prevent, minimize, or reverse the development or growth of a tumor cell.

In another preferred embodiment, a radiosensitizing composition comprises 4-N, methylamino-5-chloro-2'-deoxycytidine and a modulating dose of a cytidine deaminase inhibitor.

In another preferred embodiment, a radiosensitizing composition comprises 5-Iodo-2'-deoxycytidine with a modulating dose of a cytidine deaminase inhibitor wherein the cytidine deaminase inhibitor comprises tetrahydrouridine, or tetrahydro-2'-deoxyuridine.

In another preferred embodiment, a radiosenisitizing composition comprises 5-Bromo-2'-deoxycytidine with a modulating dose of a cytidine deaminase inhibitor wherein the cytidine deaminase inhibitor comprises tetrahydrouridine, or tetrahydro-2'-deoxyuridine.

In another preferred embodiment, a method of treating a cancer patient comprises administering to a patient a radiosensitizing or chemotherapeutic agent, in a therapeutically effective concentration, comprising: a) 4-N, methylamino-5-chloro-2'-deoxycytidine with or without a modulating dose of a cytidine deaminase inhibitor combined with or without one or more sources of radiation; b) 5-Iodo-2'-deoxycytidine with a modulating dose of a cytidine deaminase inhibitor combined with or without one or more sources of radiation; c) 5-Bromo-2'-deoxycytidine with or without a modulating dose of a cytidine deaminase inhibitor combined with or without one or more sources of radiation; d) 5-Trifluoromethyl-2'-deoxycytidine with or without a modulating dose of a cytidine deaminase inhibitor; e) 4-N, methylamino FdC with or without a modulating dose of cytidine deaminase inhibitor; and, treating a cancer patient.

In another preferred embodiment, the cancer is characterized by elevated levels of cytidine deaminase as compared to levels of cytidine deaminase in a normal individual.

In another preferred embodiment, the composition comprises 4-N, methylamino-5-chloro-2'-deoxycytidine in a pharmaceutically acceptable carrier.

In another preferred embodiment, the composition comprises 5-Iodo-2'-deoxycytidine in a pharmaceutically acceptable carrier.

In another preferred embodiment, the composition comprises 5-Bromo-2'-deoxycytidine in a pharmaceutically acceptable carrier.

In another preferred embodiment, the composition comprises 5-Trifluoromethyl-2'-deoxycytidine in a pharmaceutically acceptable carrier.

In another preferred embodiment, the composition comprises 4-N, methylamino FdC in a pharmaceutically acceptable carrier.

In another preferred embodiment, the cytidine deaminase inhibitor comprises tetrahydrouridine, tetrahydro-2'-deoxyuridine.

In another preferred embodiment, the composition is administered to a patient in an amount effective to prevent, minimize, or reverse the development or growth of a tumor in the patient upon administration to the patient.

In another preferred embodiment, the composition is delivered to a patient by slow intratumoral release, intra-muscularly, intra-venously, orally or nasally.

In another preferred embodiment, the chemotherapeutic agent or cytidine deaminase inhibitor is administered in an amount of about 1 mg/kg/individual to 50 mg/kg/individual.

In another preferred embodiment, the chemotherapeutic agent is deaminated and unsilences genes in a tumor cell which restore normal cell functions.

In another preferred embodiment, a method of treating a brain tumor comprising administering to a patient a composition comprising 4-N, methylamino-5-Cl-2'-deoxycytidine, 5-Iododeoxycytidine and 5-Bromodeoxycytidine, 5-trifluoromethyldeoxycytidine, 4-N, methylamino, and 5-fluoro-2'-deoxycytidine with or without a modulating cytidine deaminase inhibitor and with or without radiation therapy.

In another preferred embodiment, a method of treating a tumor identified by high levels of cytidine deaminase comprising administering to a patient a high dose of cytidine deaminase inhibitors comprising tetrahydrouridine F-Pyrimidine-2-one nucleoside, Diazepin-2-1-nucleoside; diazoepinone; and 2'-fluoro-2'-deoxyarabinosyl-tetrahydrouracil.

In another preferred embodiment, a method of radiosensitizing human tumors expressing high levels of uridine/cytidine kinase comprising administering to a patient a composition comprising 5-Chlorouridine and 5-Chlorocytidine with or without a cytidine deaminase inhibitor.

In another method of inhibiting the growth of human tumors possessing high levels of uridine/cytidine kinase comprising administering to a patient a composition comprising 5-fluorocytidine with or without a cytidine deaminase inhibitor.

In another preferred embodiment, the fluorocytidine hypomethylates the DNA of the tumor and generates fluorinated analogs which affect several targets selectively in the tumor.

In another preferred embodiment, a method of inhibiting the growth of tumor cells possessing high levels of uridine/cytidine kinase comprising administering to a patient or incubating a tumor cell with a pharmaceutical composition comprising 5-fluorouridine.

Other aspects of the invention are described infra.

BRIEF DESCRIPTION OF THE DRAWINGS

The invention was pointed out with particularity in the appended claims. The above and further advantages of this invention may be better understood by referring to the following descriptions in conjunction with the accompanying drawings, in which:

FIG. 1 is a schematic illustration showing the pathway of metabolism of all 5 drugs in Category 1 via cytidine deaminase (CD) and thymidine kinase. The pathway of metabolism of the five drugs (5-substituted analogs of deoxycytidine) is the only pathway available to reach their target in the tumor and it is via cytidine deaminase. Also shown is the structural formula of each of the drugs.

FIGS. 1A-1E illustrate the metabolism and targets of the five (5) drugs. FIG. 1A shows the pathway by which 4-N, methylamino CldC will be converted to a Radiosensitizer in tumors (via thymidine kinases). FIG. 1B is a schematic illustration showing the pathway by which 5-Iododeoxycytidine is converted to a Radiosensitizer in tumors (via thymidine kinase). FIG. 1C is a schematic illustration showing the pathway by which 5-Bromodeoxycytidine is converted to a Radiosensitizer in tumors (via thymidine kinase). FIG. 1D is a schematic illustration showing the pathway by which 4-N, methylamino 5-FdC generates a spectrum of fluorinated antimetabolites in pancreatic tumors (via thymidine kinase). FIG. 1E is a schematic illustration showing the pathway by which 5-Trifluoromethyl dC generates an inhibitor of thymidylate synthetase and DNA polymerase of pancreatic tumors (via thymidine kinase).

FIGS. 2 to 4 are graphs showing the potent radiosensitizing effect of 4-N, methylamino CldC in PC-3 cells (a human prostate tumor) and its antagonism by tetrahydrouridine at a concentration of 100 µM. In FIGS. 2 to 4 it can be seen that 4-N, methylamino CldC compares favorably with CldC. Radiosensitization can be achieved without extensive lethality as shown in FIG. 4.

FIGS. 2 and 3 show the radiosensitization of PC-3 cells (a human prostate tumor) by 4-N, methylamino CldC including a comparison with 5-Chlorodeocycytidine and modulating doses of H4U and the effects of high concentrations of Tetrahydrouridine (H4U). The Viability of the cells after 72 hrs of exposure is shown in this graph in parentheses and in all similar graphs summarizing results of radiation studies.

FIG. 4 shows the radiosensitization of PC-3 cells by 4-N, methylamino CldC and H4U on Viability and Radiosensitization with only moderate loss in Viability.

FIG. 12 is a graph showing radiosensitization with 5-Chlorocytidine. 5-Chlorocytidine (the riboside) including a comparison with 5-Chlorouridine in PC-3 cells. Unexpectedly H4U decreases viability of the PC-3 cells exposed to ClCyd and decreases radiosensitization by this analog. The decrease in viability may be an effect due to incorporation into RNA.

DETAILED DESCRIPTION

Figure 1B:
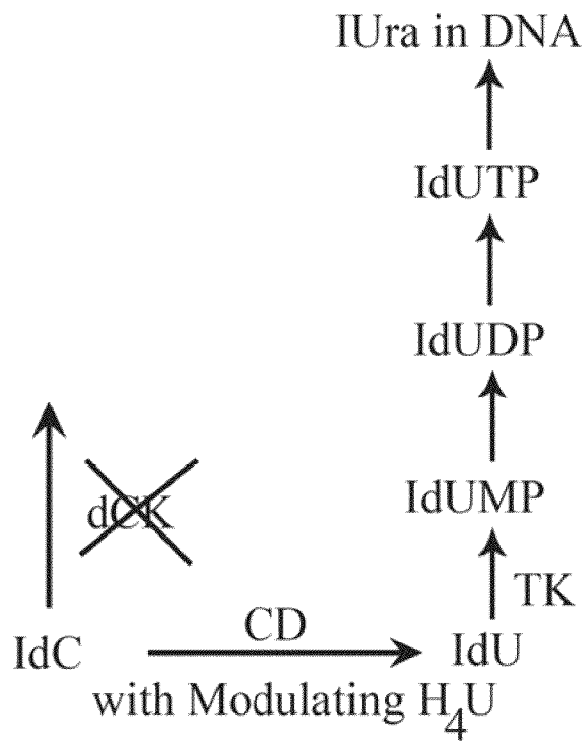

Compositions for treatment of tumors with elevated enzymes as compared to normal cells and tissues. The elevation of these enzymes are exploited for a therapeutic advantage. The drugs of this invention are poorly activated or not activated by deoxycytidine kinase (Table C) and cannot be activated by thymidine kinase unless they are deaminated by cytidine deaminase for which they are substrates (Table D). Methods of treating such tumors can include cytidine deaminase inhibitors, other chemotherapeutic agents and radiation therapy.

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

DEFINITIONS

In accordance with the present invention and as used herein, the following terms are defined with the following meanings, unless explicitly stated otherwise.

As used herein, "a", "an," and "the" include plural references unless the context clearly dictates otherwise.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and therapeutic effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical salt" include, but are not limited to, mineral or organic acid salts of basic residues such as amines; alkali or organic salts of acidic residues such as carboxylic acids. Preferably the salts are made using an organic or inorganic acid. These preferred acid salts are chlorides, bromides, sulfates, nitrates, phosphates, sulfonates, formates, tartrates, maleates, malates, citrates, benzoates, salicylates, ascorbates, and the like. The most preferred salt is the hydrochloride salt.

As used herein, "cancer" refers to all types of cancer or neoplasm or malignant tumors found in mammals, including, but not limited to: leukemias, lymphomas, melanomas, carcinomas and sarcomas.

As used herein, the terms "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

The term "modulating dose of tetrahydrouridine" means a dose which prevents premature systemic deamination of the drug before it reaches the tumor site and dose that will inhibit the CD of normal tissue to a greater extent than the CD of the tumor. This will also prevent the systemic catabolism of the drug.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests. For example, the "treatment of cancer" or "tumor cells", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "an ameliorated symptom" or "treated symptom" refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values. Modulation can also decrease its activity below baseline values, such as for example, partial inhibition (e.g. 5%, 10%, 20%, 25% as compared to controls) or complete inhibition as compared to controls.

As used herein, the term "selective for tumor cells" refers to the effects of the instant pharmaceutical compositions, such as inhibition of tumor growth, apoptosis, anti-angiogenic effects, inhibition of repair, greater tumor kill, reactivation of tumor suppressor or repair genes, and which are not detectable when applied to normal cells, as described in detail in the examples which follow.

Anti-Cancer Compositions

A study of tumor and associated normal tissue of 220 patients with cancer of the head and neck, colon/rectum, brain, lung, breast and, most recently, pancreas, with respect to 4 enzymes of pyrimidine metabolism resulted in a surprising discovery: 90% of the 40 pancreatic tumors examined displayed pronounced elevation of only one of the four enzymes—cytidine deaminase (CD). 66% and 40% of the patients had a >4 and >6-fold respective increase in the enzyme above adjacent normal tissue. No other tumor displayed this marked elevation (although colorectal tumors were close). This increase can be exploited for a therapeutic advantage with 5 novel deoxycytidine analogs, never before used in man. Three are radiosensitizers:

Category I Drug:
a) 4-N, methylamino-5-Chloro-2'-deoxycytidine
X=H—N—CH$_3$ Y=Cl
b) 5-Iodo-2'-deoxycytidine
X=H—N—H Y=I
c) 5-Bromo-2'-deoxycytidine
X=H—N—H Y=Br
and two are Chemotherapeutic Agents:
a) 4-N, methylamino-5-Fluoro-2'-deoxycytidine
X=H—N—CH$_3$ Y=F
b) 5-Trifluoromethyl-2'-deoxycytidine
X=H—N—H Y=CF$_3$ This drug was shown in studies to be superior to 5-FUra, 5-FdU and 5-F3dT vs a mouse tumor.

The drugs are metabolized to be incorporated into tumor DNA and/or inhibit the key target enzyme, thymidylate synthetase, only via the cytidine deaminase pathway. Radiosensitization and toxicity in cell culture is reversed by tetrahydrouridine, an inhibitor of CD or by thymidine, their antagonist.

Category II drugs: These are inhibitors of cytidine deaminase and include: Tetrahydrouridine, F-Pyrimidine-2-one nucleoside, Diazepin-2-1-nucleoside; diazoepinone; 2'-fluoro-2'-deoxyarabinosyl-tetrahydrouracil.

In a preferred embodiment, the tumors, for example pancreatic tumors, are uniquely sensitive to inhibitors of CD, an enzyme which may play a role in their aggressiveness.

In another preferred embodiment, a radiosensitizing agent or composition comprises any one or more of 4-N, methylamino-5-chloro-2'-deoxycytidine with or without a modulating dose of a cytidine deaminase inhibitor combined with or without one or more sources of radiation; 5-Iodo-2'-deoxycytidine with a modulating dose of a cytidine deaminase inhibitor combined with or without one or more sources of radiation; 5-Bromo-2'-deoxycytidine with or without a modulating dose of a cytidine deaminase inhibitor combined with or without one or more sources of radiation.

In another preferred embodiment, a chemotherapeutic agent comprises 5-Trifluoromethyl-2'-deoxycytidine with or without a modulating dose of a cytidine deaminase inhibitor.

In another preferred embodiment, a chemotherapeutic agent comprises 4-N, methylamino FdC with or without a modulating dose of a CD inhibitor. This drug was synthesized within the context of it acting as a hypomethylating agent via its activation by deoxycytidine kinase. It is not, however, a substrate for deoxycytidine kinase and it is not a hypomethylating agent.

Any and all of the treatments herein can be combined with any known therapies such as radiation, chemotherapy, anti-angiogenic drugs, cytokines, chemokines and the like.

In another preferred embodiment, the tumor is characterized by elevated levels of cytidine deaminase as compared to levels of cytidine deaminase in a normal cell or tissue.

In one embodiment, the measurement of cytidine deaminase levels is predictive and diagnostic of a tumor or progression to such. The levels of cytidine deaminase can be a predictor of pre-metastatic or metastatic tumor.

In one preferred embodiment, the composition comprises 4-N, methylamino-5-chloro-2'-deoxycytidine in a pharmaceutically acceptable carrier.

In another preferred embodiment, the composition comprises 5-Iodo-2'-deoxycytidine in a pharmaceutically acceptable carrier.

In another preferred embodiment, the composition comprises 5-Bromo-2'-deoxycytidine in a pharmaceutically acceptable carrier.

In another preferred embodiment, the composition comprises 5-Trifluoromethyl-2'-deoxycytidine in a pharmaceutically acceptable carrier.

In another preferred embodiment, the composition comprises 4-N, methyl FdC in a pharmaceutically acceptable carrier.

In another preferred embodiment, a source of radiation comprises X-rays, γ-rays, protons, brachytherapy, yttrium-90, β-rays, x-mesons, monoclonal antibodies attached to Radionuclides, stereotactic radio surgery, 3-Dimensional Conformal Radiation and Intensity Modified Radiation Therapy.

In another preferred embodiment, a cytidine deaminase inhibitor comprises tetrahydrouridine, tetrahydro-2'-deoxyuridine F-Pyrimidine-2-one nucleoside, Diazepin-2-1-nucleoside; diazoepinone; 2'-fluoro-2'-deoxyarabinosyl-tetrahydrouracil.

In certain embodiments, the composition of the present invention may be administered in combination with another chemotherapeutic agent. Irrespective of the underlying mechanism(s), a variety of chemotherapeutic agents may be used in the combined treatment methods disclosed herein. Therapeutic agents can include, for example, chemotherapeutic agents such as, cyclopliosphamide (CTX, 25 mg/kg/day, p.o.), taxanes (paclitaxel or docetaxel), busulfan, cisplatin, methotrexate, daunorubicin, doxorubicin, melphalan, cladribine, vincristine, vinblastine, chlorambucil, tamoxifen, taxol, etoposide (VP-16), adriamycin, 5-fluorouracil (5FU), camptothecin, actinomycin-D, mitomycin C, cisplatin (CDDP), combretastatin(s) and derivatives and prodrugs thereof.

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally. Timing of administration is important because radiosensitizers and chemotherapeutic agents require DNA synthesis for their effectiveness.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

The skilled artisan is directed to "Remington's Pharmaceutical Sciences" 15th Edition, chapter 33, in particular pages 624-652, for non-limiting examples of other chemotherapeutic agents that can be used in combination therapies with the instant compositions. Some variation in dosage will necessarily occur depending on the condition of the subject being treated. The physician responsible for administration will be able to determine the appropriate dose for the individual subject.

Anti-angiogenics: The term "angiogenesis" refers to the generation of new blood vessels, generally into a tissue or organ. Under normal physiological conditions, humans or animals undergo angiogenesis only in very specific restricted situations. For example, angiogenesis is normally observed in wound healing, fetal and embryonic development and formation of the corpus luteum, endometrium and placenta. Uncontrolled (persistent and/or unregulated) angiogenesis is related to various disease states, and occurs during tumor growth and metastasis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

As persistent, unregulated angiogenesis occurs during tumor development and metastasis, the treatment methods of this invention may be used in combination with any one or more "anti-angiogenic" therapies. It should be noted that irradiation of a tumor destroys the tumor capillary bed which would complement an anti-angiogenesis strategy.

Subject

Because subjects from many different species have tumors and are susceptible to acquiring a tumor, the invention is compatible with many types of animal subjects. A non-exhaustive exemplary list of such animals includes mammals such as mice, rats, rabbits, goats, sheep, pigs, horses, cattle, dogs, cats, and primates such as monkeys, apes, and human beings. Those animal subjects known to suffer from a skin cancer tumor are preferred for use in the invention. In particular, human patients suffering from a skin cancer tumor or other tumors are suitable animal subjects for use in the invention. By adapting the methods taught herein to other methods known in medicine or veterinary science (e.g., adjusting doses of administered substances according to the weight of the subject animal), the compositions utilized in the invention can be readily optimized for use in other animals.

Pharmaceutical Compositions and Administration to a Subject

The composition of the invention can be administered to a patient either by themselves, or in pharmaceutical compositions where it is mixed with suitable carriers or excipient(s). In treating a patient exhibiting a disorder or interest, a therapeutically effective amount of a agent or agents such as these is administered. A therapeutically effective dose refers to that amount of the compound that results in amelioration of symptoms or a prolongation of survival in a patient. It should be noted that since the drugs are prodrugs which are resistant to catabolism, oral administration is one of the preferred embodiments.

In a preferred embodiment, the compositions are delivered by slow intratumoral release. They may be delivered with polymers such as bis(p-carboxyphenoxy) propane-sebacic acid or by perfusion.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC. $F_3$methyldC has been studied in mice (Mekras J., Boothman D. and Greer S. *Cancer Res.* 45:5270-5280, 1985 which is incorporated herein by reference in its entirety) and the toxicity data are available.

The exact formulation, route of administration and dosage can be chosen by the individual physician in view of the patient's condition. (See e.g. Fingl et al., in The Pharmacological Basis of Therapeutics, 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, or intestinal administration, parenteral delivery, including intramuscular, subcutaneous, intramedullary injections, as well as intrathecal, direct intraventricular, intravenous, intraperitoneal, intranasal, or intraocular injections, just to name a few.

The compositions described above may be administered to a subject in any suitable formulation. For example, the compositions can be formulated for parenteral delivery, e.g., for subcutaneous, intravenous, intramuscular, or intratumoral injection. Other methods of delivery, for example, liposomal delivery or diffusion from a device impregnated with the composition might be used. The compositions may be administered in a single bolus, multiple injections, or by continuous infusion (for example, intravenously or by peritoneal dialysis). For parenteral administration, the compositions are preferably formulated in a sterilized pyrogen-free form. Compositions of the invention can also be administered in vitro to a cell (for example, to radiosensitize a cancer cell in an in vitro culture) by adding the composition to the fluid in which the cell is contained.

Depending on the specific conditions being treated, such agents may be formulated and administered systemically or locally. Techniques for formulation and administration may be found in Remington's Pharmaceutical Sciences, 18$^{th}$ ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors especially for tetrahydrouridine which is acid labile and should be degraded by stomach acids. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Formulations suitable for topical administration for dermatological tumors or a slow release for systemic distribution include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinyl pyrrolidone (PVP). If desired, disintegrating agents may be added, such as the cross-linked polyvinyl pyrrolidone, agar, or alginic acid or a salt thereof such as sodium alginate.

Dragee cores are provided with suitable coating. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The composition can include a buffer system, if desired. Buffer systems are chosen to maintain or buffer the pH of compositions within a desired range. The term "buffer system" or "buffer" as used herein refers to a solute agent or agents which, when in a water solution, stabilize such solution against a major change in pH (or hydrogen ion concentration or activity) when acids or bases are added thereto. Solute agent or agents which are thus responsible for a resistance or change in pH from a starting buffered pH value in the range indicated above are well known. While there are countless suitable buffers, potassium phosphate monohydrate is a preferred buffer.

The final pH value of the pharmaceutical composition may vary within the physiological compatible range. Necessarily, the final pH value is one not irritating to human skin and preferably such that transdermal transport of the active compound, is facilitated. Without violating this constraint, the pH may be selected to improve compound stability and to adjust consistency when required. In one embodiment, the preferred pH value is about 3.0 to about 7.4, more preferably about 6.5 to about 7.4, more preferably from about 7.2 to about 7.4. For example, tetrahydrouridine is preferably kept at pH 7.2 to 7.4.

For preferred topical delivery vehicles the remaining component of the composition is water, which is necessarily purified, e.g., deionized water. Such delivery vehicle compositions contain water in the range of more than about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle preferably has a viscosity of at least about 30 centipoises.

Other known transdermal skin penetration enhancers can also be used to facilitate delivery. Illustrative are sulfoxides such as dimethylsulfoxide (DMSO) and the like; cyclic amides such as 1-dodecylazacycloheptan-2-one (AZONE™, a registered trademark of Nelson Research, Inc.) and the like; amides such as N,N-dimethyl acetamide (DMA) N,N-diethyl toluamide, N,N-dimethyl formamide, N,N-dimethyl octamide, N,N-dimethyl decamide, and the like; pyrrolidone derivatives such as N-methyl-2-pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallowalkylpyrrolidones, and the like; polyols such as propylene glycol, ethylene glycol, polyethylene glycol, dipropylene glycol, glycerol, hexanetriol, and the like; linear and branched fatty acids such as oleic, linoleic, lauric, valeric, heptanoic, caproic, myristic, isovaleric, neopentanoic, trimethyl hexanoic, isostearic, and the like; alcohols such as ethanol, propanol, butanol, octanol, oleyl, stearyl, linoleyl, and the like; anionic surfactants such as sodium laurate, sodium lauryl sulfate, and the like; cationic surfactants such as benzalkonium chloride, dodecyltriethylammonium chloride, cetyltrimethylammonium bromide, and the like; non-ionic surfactants such as the propoxylated polyoxyethylene ethers, e.g., Poloxamer 231, Poloxamer 182, Poloxamer 184, and the like, the ethoxylated fatty acids, e.g., Tween 20, Myrj 45, and the like, the sorbitan derivatives, e.g., Tween 40, Tween 60, Tween 80, Span 60, and the like, the ethoxylated alcohols, e.g., polyoxyethylene (4) lauryl ether (Brij 30), polyoxyethylene (2) oleyl ether (Brij 93), and the like, lecithin and lecithin derivatives, and the like; the terpenes such as D-limonene, α-pinene, β-carene, α-terpineol, carvol, carvone, menthone, limonene oxide, α-pinene oxide, eucalyptus oil, and the like.

Also suitable as skin penetration enhancers are organic acids and esters such as salicyclic acid, methyl salicylate, citric acid, succinic acid, and the like.

Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application were incorporated by reference in pertinent part for all purposes to the same extent as if each individual publication or patent document were so individually denoted. By their citation of various references in this document, Applicants do not admit any particular reference was "prior art" to their invention.

EXAMPLES

The following examples serve to illustrate the invention without limiting it thereby. It will be understood that variations and modifications can be made without departing from the spirit and scope of the invention.

Materials and Methods

Deoxycytidine Kinase (dC Kinase) Activity: The tissue was suspended in a buffer containing 50 mM Tris HCl (pH 7.5), 5 mM benzamidine, 20% glycerol, 0.5% IGEPAL (octylphenoxy)polyethoxyethanol, and 52% $H_2O$. 2 mM dithiothreitol (DTT) and 0.5 mM phenylmethylsulfanyl fluoride were added just before extraction. The tissue sample was homogenized in a Dounce glass homogenizer and then sonicated for 3 five-second pulses in a Branson Sonifier with a micro-tip at 25 KHz to disrupt the cells. During homogenization and sonication the extract was kept cold throughout the procedures. The tissue extract was then centrifuged at 14,000×g at 4° C. for 15 min., and the supernatant (the crude enzyme extract) was removed. The supernatant was sheared 20 times on ice utilizing a 1 cc syringe with a 27 G½ needle to reduce viscosity. The reaction mixture contained 50 mM Tris HCl (pH 7.5), 50 mM $MgCl_2$, 5 mM ATP, 10 mM NaF and 85% $H_2O$. 2 mM DTT and 340 μM H4U were added just before the assay. Finally, to the reaction mixture, 5 μl 200 mM creatine phosphate and creatine phosphokinase (0.5 unit/μl) was added to 150 μl of the section mixture. After pre-incubation for 2 minutes at 37° C., $^3$H-deoxycytidine was added to the assay mixture to a final concentration of 50 μM and placed in a 37° C. $H_2O$ bath for 1 minute before 20 μl of the crude enzyme extract was added to initiate the reaction. The reaction was linear for 60 minutes. At 0, 30 and 60 minutes the reaction mixture, divided in separate tubes, was heated in a boiling water bath for 2 minutes to terminate the reaction. Denatured protein was then removed by centrifugation of the sample for 2 minutes at 14,000×g. The amount of nucleotide formed was determined by spotting 20 μl aliquots of the reaction mixture onto DE-81 2.2 cm Whatman filter discs. After air drying, the unphosphorylated substrate nucleoside was removed by washing twice for 10 min. in 20 mM ammonium formate and twice for 5 min. in deionized $H_2O$ with gentle stirring. A control, lacking the crude enzyme extract was included with each determination. The washed papers were dried under a heat lamp and then placed into individual scintillation vials, eluted for 30 min. in 1 ml of 0.1M HCl-0.1M KCL and then vortexed in 5 ml of scintillation fluid and counted. Enzyme activity was expressed as pmoles/min/mg protein.

Uridine/cytidine kinase Activity: This assay was identical to the deoxycytidine kinase assay when cytidine was utilized. When uridine was utilized as substrate, benzacyclouridine was added to prevent the catabolism of the substrate by uridine phosphorylase and tetrahydrouridine was omitted.

Thymidine kinase Activity: This assay was identical to the deoxycytidine kinase assay except that $^3$H-thymidine was utilized and tetrahydrouridine was omitted.

dCMP Deaminase Activity: The crude enzyme extract was prepared as described in A. The reaction was carried out in 60 mM Tris HCl, pH 8.0, and 50 μm dCTP, 2.5 mM MgCl$_2$, 30 mM NaF, and 80% H$_2$O to which dCMP ($^3$H labeled) was added to a final concentration of 2 mM; 20 μl of enzyme extract was added to initiate the reaction giving a total volume of 20 μl. The reaction was linear for 30 minutes at 37° C. A control lacking enzyme was included with each determination. The reaction was terminated as described above in at 0, 30 and 45 minutes and denatured protein was removed by centrifugation as described above. To 10 μl of the supernatant, 6 μl of a 0.03M solution of the carrier nucleotides, dCMP and dUMP were added so that the reactants can be visualized under a UV lamp. Chromatographic isolation of the products was carried out in 2 different solvent systems: A) Baker DEAE Cellulose TLC sheets in 0.01N HCl for 35 min. Rf dCMP and dUMP: 0.42 and 0.26, respectively and B) Analtech Cellulose TLC sheets with isopropanol:HCl:H$_2$O (in a ratio of 4:1:2) for 6.5 hours. Rf dCMP and dUMP: 0.68 and 0.84, respectively. Each appropriate area of the thin layer sheets (where dCMP and dUMP were separated), were cut into small pieces and placed in separate vials and extracted with 1N HCl (1 ml) for 30 minutes. Scintillation cocktail was added (5 ml) to the vials which were vortexed prior to counting. The specific activity was expressed as nmoles/min/mg protein.

Cytidine deaminase Activity: The crude extract was prepared as above for dC Kinase; however, when cytidine was used as substrate, as soon as aliquots of the supernatant were separated for the other enzyme assays, 200 μM UTP was added, presumably to inhibit uridine/cytidine kinase activity. When sufficient material was available, cytidine deaminase activity was determined using both cytidine and deoxycytidine as substrates. The reaction mixture contained 25 mM Tris-HCl (pH 8.0), 5 mM MgCl$_2$ and 10 mM NaF (to inhibit phosphorylases activity.) $^3$H-cytidine or $^3$H-deoxycytidine was added to the reaction mixture to a final concentration of 50 μM and incubated at 37° C. for 1 minute. The crude enzyme extract (the supernatant of a 10 minute 14,000×g centrifugation) was then added. When cytidine was used as substrate, assays were conducted with benzacyclouridine to inhibit uridine phosphorylases. The reaction was linear for 30 minutes at 37° C. After 0, 15, and 30 minutes, the reaction was stopped and denatured protein removed as above for dC Kinase. 6 μl of 0.03M carrier nucleoside (cytidine or deoxycytidine and uridine or deoxyuridine, respectively), was added to 10 μl of the supernatant. Aliquots were then spotted on PE cellulose TLC sheets and the reactants separated with a solvent system composed of isopropanol:HCl:H$_2$O (170: 41:39). The Rfs of cytidine and uridine were 0.46 and 0.69 respectively; the Rfs of deoxycytidine and deoxyuridine were 0.62 and 0.84 respectively after 7½ hrs. The nucleosides were visualized under U.V. light and the spots cut out and counted. In addition to a 0 time and a no-extract control, the assay was run with the addition of H4U, the potent inhibitor of cytidine deaminase, as a control. Enzyme activity was expressed as nmole formed in 30 min/mg/protein.

Protein concentrations for the above assays were determined by the Bradford method, buffer as the blank and serum albumin as the standard.

All determinations utilized a benzene based scintillant composed of 10-20% docusate sodium, 2.5-10% ethoxylated alkylphenol, 60-80% benzene, C10-13-alkyl derivatives, ≦2.5% 2,5-diphenyloxazole, and ≦2.51% 1,4-bis(4-methyl-alpha-styryl)benzene, using a Beckman LS-5000 counter.

Competition assays to determine Substrate Specificity: Crude extracts of PC-3 cells in culture were prepared as described above. Two concentrations of crude extract were utilized for the studies as determined from the analysis of protein. There was a 5-fold difference between the two concentrations and was usually in the range of 0.15 to 0.25 and 0.15/5 to 0.25/5 mg/ml.

The concentration of $^3$H-cytidine or $^3$H-deoxycytidine used for the cytidine deaminase competition assay was 50 mM and the concentration of unlabelled candidate competitor was usually 2, 5, 10 and 20-fold higher than the tritiated substrate. The assays were run for 0, 15, and 30 minutes. The assays were always run with a 'no drug' addition to obtain a baseline and an established positive control (such as cytidine or deoxycytidine) and a negative control (such as uridine or thymidine).

The competition assay for substrates of deoxycytidine kinase was similar to that described above except for the use of only $^3$H-deoxycytidine as substrate. Tetrahydrouridine was added and 5-benzacyclouridine was omitted. The assays were run for 0, 30, and 60 minutes and the positive control was either deoxycytidine or 5-chlorodeoxycytidine and the negative control was either cytidine or uridine.

Toxicity and Radiation Studies: The methods using clonogenic assays described by Perez and Greer (*Int. J. Rad. Oncology: Biology, Physics* 12, 1523-1527, 1986—incorporated herein by reference in its entirety) were followed.

Cytotoxicity Assays: 5×10$^5$ cells were plated in 60 mm tissue culture dishes in 5 mls of the optimal growth media for the particular cell line in an humidified 95% air-5% CO$_2$ atmosphere. The plates were incubated for 18-20 hours to allow for attachment and log-phase growth to begin. At the end of this period the growth medium was aspirated and replaced with 4 mls of drug-containing media. Four times (4×) concentrated solutions were prepared and then 1 ml was added to the plates; and growth media were then added to a total volume of 5 mls. The plates were then incubated for 72 hours and the cells harvested by trypsinization. The cells were then serially diluted in growth medium replated into 60 mm dishes and incubated for 6 to 9 days depending on the cell line. After this incubation period, the media was aspirated and the colonies were washed twice with a PBS solution. The colonies were then stained with a 0.2% crystal violet-20% ethanol solution for 5 min. the stain was removed, the colonies were washed and air dried. A viable colony was one consisting of 25 or more normal appearing cells and was considered to have arisen from a single cell. The colonies were counted under a dissecting microscope. Two to three dilutions for every condition were plated. Dishes containing 30-300 colonies were used in the calculation and all conditions were done in duplicate.

Irradiation of Cells in Culture: 2×10$^5$ cells were plated in 25 cm$^2$ flasks and grown for 18 hr at 37° C. in a humidified 5%

$CO_2$ atmosphere. The medium was then removed and replaced with medium containing the appropriate drug concentrations and incubated for 72 hrs then removed and the cell monolayers were rinsed twice with PBS. The flasks were then filled with 50 ml of radiation medium (3 parts RPMI 1640 and 7 parts PBS plus antibiotics and glutamine). The cells were then irradiated using a Cobalt 60 irradiator. The cell monolayers were placed 35 cm away from the source and irradiated for appropriate times according to the dose rate. The dose rate was calculated, at this distance, using ionization chambers. Attenuation factors due to the polystyrene flask (0.9923) and the medium ($H_2O$=0.8715) were considered in calculating the exposure period.

After irradiation the cell monolayers were washed again, replenished with growth media, and incubated for 1½ hours. The cell monolayers were then trypsinized and the cells serially diluted, appropriate dilutions were then plated in 60 mm dishes and incubated for 7-9 days at 37° C. and $CO_2$. At the end of this period the cells were stained with crystal violet and the colony forming ability determined by considering 25 or more normal cells as a viable colony. The viabilities were determined and the appropriate survival curves derived. All conditions were done in duplicate using two flasks treated under identical conditions.

Example 1

Designer Therapy of Pancreatic Tumors Based on the Frequency of Elevation of Cytidine Deaminase in Patients with Cancer of the Pancreas Allowing Enzyme-Driven Selective Target-Directed Radiation—and Chemotherapy Coupled with Gene Unsilencing with Novel Drugs Not Heretofore Used in Man In an enzymological study of forty pancreatic tumors and adjacent normal pancreatic tissue, from patients with pancreatic cancers, with respect to four enzymes of pyrimidine metabolism, an unexpected elevation of one of the four enzymes above that of adjacent normal tissue in the patients was found. The four enzymes studied are: deoxycytidine kinase (dCK), dCMP deaminase (dCMPD), uridine/cytidine kinase (U/CK) and cytidine deaminase (CD) and thymidine kinase. It is the latter enzyme, cytidine deaminase, which is dramatically and almost uniquely elevated.

To emphasize the uniqueness of this unanticipated elevation, only 6/50, 18/40 and 13/40 patients with this tumor were elevated >2-fold over normal tissue for dCK, dCMPD and U/CK, respectively, whereas 34/40 were elevated >2-fold for CD. The frequency of elevations of >4-fold was 0/40, 0/40, and 6/40 for dCK, dCMPD and U/CK respectively, yet 25/40 patients were elevated greater than 4-fold for CD. Furthermore, 17/40 patients were elevated greater than 6-fold for CD, in sharp contrast, the frequency of a 6-fold T/N was 0/40, 0/40 and 1/40 for dCK, dCMPD and U/CK respectively. This data is shown under T/N ratio in Table B.

In addition to these surprising findings was the observation that in ten of the forty patients neither dCK, dCMPD nor U/CK were elevated (Tumor Specific Activity/Normal Specific Activity=1) while CD was the only enzyme elevated significantly and markedly.

Table C shows that none of the 5 drugs are substrates for deoxycytidine kinase whereas, as shown in Table D, they are good substrates for cytidine deaminase as determined in competition studies with deoxycytidine or with cytidine as substrate; 4-N, methylamino FdC appears to be a poor substrate yet its cytotoxicity was antagonized by tetrahydrouridine. These competition studies were undertaken with crude extracts of PC-3, a human prostate cancer cell line.

Table E summarizes a toxicity study with PC-3 cells in which it is shown that the cytotoxicity of IdC and 5-$F_3$methyldC is antagonized by Tetrahydrouridine, consistent with the mechanism of the metabolism of 5-iododeoxycytidine and 5-trifluoromethyl deoxycytidine being via the cytidine deaminase pathway. Results not included in the table show that the cytotoxicity was antagonized by thymidine.

TABLE A

A comparison of the marked elevation of cytidine deaminase (CD) in pancreatic tumors over that of normal tissue with the moderate increase of 4 other enzymes: deoxycytidine kinase (dCK), dCMP deaminase (dCMPD) and uridine/cytidine kinase (U/CK), including recent studies with thymidine kinase (TK).

| | Specific Activity | | | | | | | | | | T/N Ratio | | | | | |
|---|---|---|---|---|---|---|---|---|---|---|---|---|---|---|---|---|
| | dCK | | dCMPD | | U/CK | | CD | | TK | | | dCK | dCMPD | U/CK | CD | TK |
| | T | N | T | N | T | N | T | N | T | N | n | 40 | 40 | 40 | 40 | 12 |
| n | 40 | 24 | 40 | 24 | 40 | 24 | 40 | 24 | 13 | 5 | >1.5 | 11 | 23 | 17 | 36 | 5 |
| min | 6.2 | 5.4 | 1.1 | 0.57 | 5.2 | 9.4 | 1 | 0.6 | 2.9 | 7.4 | >2 | 6 | 18 | 13 | 33 | 3 |
| mean | 23 | 20 | 14 | 9.2 | 160 | 110 | 20 | 2.9 | 29 | 28 | >4 | 0 | 0 | 4 | 27 | 0 |
| max | 55 | 52 | 38 | 21 | 600 | 590 | 61 | 12 | 64 | 57 | >6 | 0 | 0 | 1 | 16 | 0 |

T/N: ratio of enzyme activity in tumor/enzyme activity in normal adjacent tissue. T/N for 14 tumors determined by averaging 24 tumors for the normal value.
dCK, U/CK: nmoles/min/mg protein.
dCMPD: pmoles/min/mg protein.
CD: pmoles/30 min/mg/protein.
n: number of tissues examined.

Thirty one pancreatic tumors were Ademocarcinoma, four were Intraductal, four were Neurendocrine and one was Angiolmphatic.

TABLE B

A comparison of the frequency of pancreatic tumors having a T/N value >4 with the frequency found for dCK, dCMPD, U/CK as well as CD in tumors of the lung, rectum, breast, brain and tumors of the head and neck demonstrating the unique nature of the findings with the pancreatic tumors.

| Tumor | T/N ≧ 4 for CD (%) | T/N ≧ 4 for dCK (%) | T/N ≧ 4 for dCMPD (%) | for U/CK T/N ≧ 4% |
|---|---|---|---|---|
| SCC of Lung | 6/28 (21) | 3/37 (8) | 7/37 (19) | 18/36 (50) |
| Adeno of Lung | 1/16 (6.3) | 0/16 (0) | 4/16 (25) | 5/16 (31) |
| Adeno of Rectum | 10/19 (53) | 5/24 (21) | 12/24 (50) | 15/23 (65) |
| Breast | 8/29 (28) | 13/30 (43) | 22/30 (73) | 19/28 (68) |
| Brain | 5/16 (31) | 0/17 (0) | 8/17 (47) | 3/17 (18) |
| Head & neck | Not done | 11/24 (46) | 14/24 (58) | Not done |
| Pancreas | 27/40 (68) | 0/40 (<0.03) | 0/40 (<0.03) | 4/40 (10) |

TABLE C

Capacity of nucleoside analogs to serve as substrates for dCK as determined in competition studies with extracts of PC-3 cells (a human prostate cell line).

| Nucleoside Competitor 250 μM | Ratio: Competitor/Substrate [25] Substrate $^3$H-Deoxycytidine (10 μM) % Inhibition |
|---|---|
| 5-Chlorodeoxycytidine | 72 |
| Deoxycytidine | 87 |
| 5-Fluorodeoxycytidine | 90 |
| 4-N,methylamino FdC; 4-N methylamino CldC | 0* |
| 5-TrifluoromethyldC; 5-BrdC; 5-IdC | 0* |

0* = Value equal or greater than 'No Drug' Control

TABLE D

Capacity of nucleoside analogs to serve as substrates for CD as determined in competition studies with extracts of PC-3 cells in culture.

| | Ratio: Competitor/Substrate [10] Type of Assay | | Competitor/Substrate [25] |
|---|---|---|---|
| | Cytidine Deaminase (CD) | | Deoxycytidine kinase (dCK) |
| Nucleoside Competitor (μM 250) | Substrate $^3$H-Deoxycytidine (25 μM) % Inhibition | Substrate $^3$H-Cytidine (25 μM) % Inhibition | Substrate $^3$H-Deoxycytidine (10 μM) % Inhibition |
| 5-Chlorodeoxycytidine | 42 | 80 | 72 |
| 4-N,methylamino CldC | 29 | 13 | 0* |
| 4-N,methylamino FdC | 4.0 | 0 | — |
| 5.TrifluoromethyldC | 69 | 26 | 0* |
| 5.IdC | 60 | 47 | 0* |
| 5.BrdC | — | 50 | 0* |
| 5-methyldC | — | 30 | 80 |
| 5-FdC | 50 | 83 | 90 |
| Deoxycytidine | 66 | 68 | 87 |
| Cytidine | 85 | 74 | 0* |
| Uridine | 2.0 | — | 0* |

0* = Value equal or greater than No Drug Control

TABLE E

The Reversal of the Cytotoxicity of 5-Iododeoxycytidine (Idc) and 5-Trifluoromethyl Deoxycytidine (F3methyldC) by Tetrahydrouridine ($H_4U$)

| Nucleoside | μM | $H_4U$ μM | % S |
|---|---|---|---|
| None | 0 | 0 | — |
| None | 0 | 100 | 100 |
| 5-IdC | 5 | 0 | 15 |
| | 5 | 5 | 100 |
| | 10 | 5 | 53 |
| | 20 | 5 | 30 |
| 5-IdC | 5 | 100 | 97 |
| | 10 | 100 | 73 |
| | 20 | 100 | 65 |
| 5-IdC | 5 | 1500 | 100 |
| | 10 | 1500 | 89 |
| | 20 | 1500 | 61 |
| 5-CF$_3$dC | 1 | 5 | 67 |
| | 1 | 100 | 100 |
| | 1 | 1500 | 100 |
| | 10 | 5 | 0.1 |
| | 10 | 100 | 2 |
| | 10 | 1500 | 3.3 |

In Table B, only the dCMPD (and dCK) of breast tumors and head and neck tumor approach the >4 T/N % obtained for pancreatic tumors, however, the therapy involving dCK and dCMPD (5-chloro-2'-deoxycytidine) requires that both enzymes be elevated for the strategy of radiosensitization with the analog (Greer, S., et al. *Int. J. Rad. Oncol. Biol. Phys.* 51: 791-906 (2001); Greer, S., et al. *Miami Nature Biotechnology Winter Symposium* 14:55 (2003)). The value for T/N>4 of both enzymes was 13/30 (43%) for breast tumors—certainly a high number, but far from a value of 68%. Both enzymes were elevated >4-fold in 8/24 (33%) in Head and Neck tumors.

Novel Therapy—(Radiosensitization)

4-N, methylamino-5-Chloro-2'-deoxycytidine: 4-N, methylamino-5'-chlorodeoxycytidine which has been, unexpectedly, found to be a very poor substrate for deoxycytidine kinase (dCK) Table C, but a reasonably good substrate for cytidine deaminase (CD) (Table D). Tables C and D summarize competition studies with crude extracts of human tumor cells in culture. These studies with normal metabolites and other analogs for comparison, are reliable indicators of substrate specificity. The drugs were tested with two concentrations of crude extract to make certain that the amount of enzyme was on the linear portion of the activity curve.

The results described above indicate that the only effective pathway for the metabolism of this drug is via deamination by cytidine deaminase to CldU and then conversion to CldUMP→CldUDP→CldUTP by thymidine kinase and the higher kinases incorporation into DNA as a radiosensitizer. See FIGS. 1 and 1A.

Figure 3:
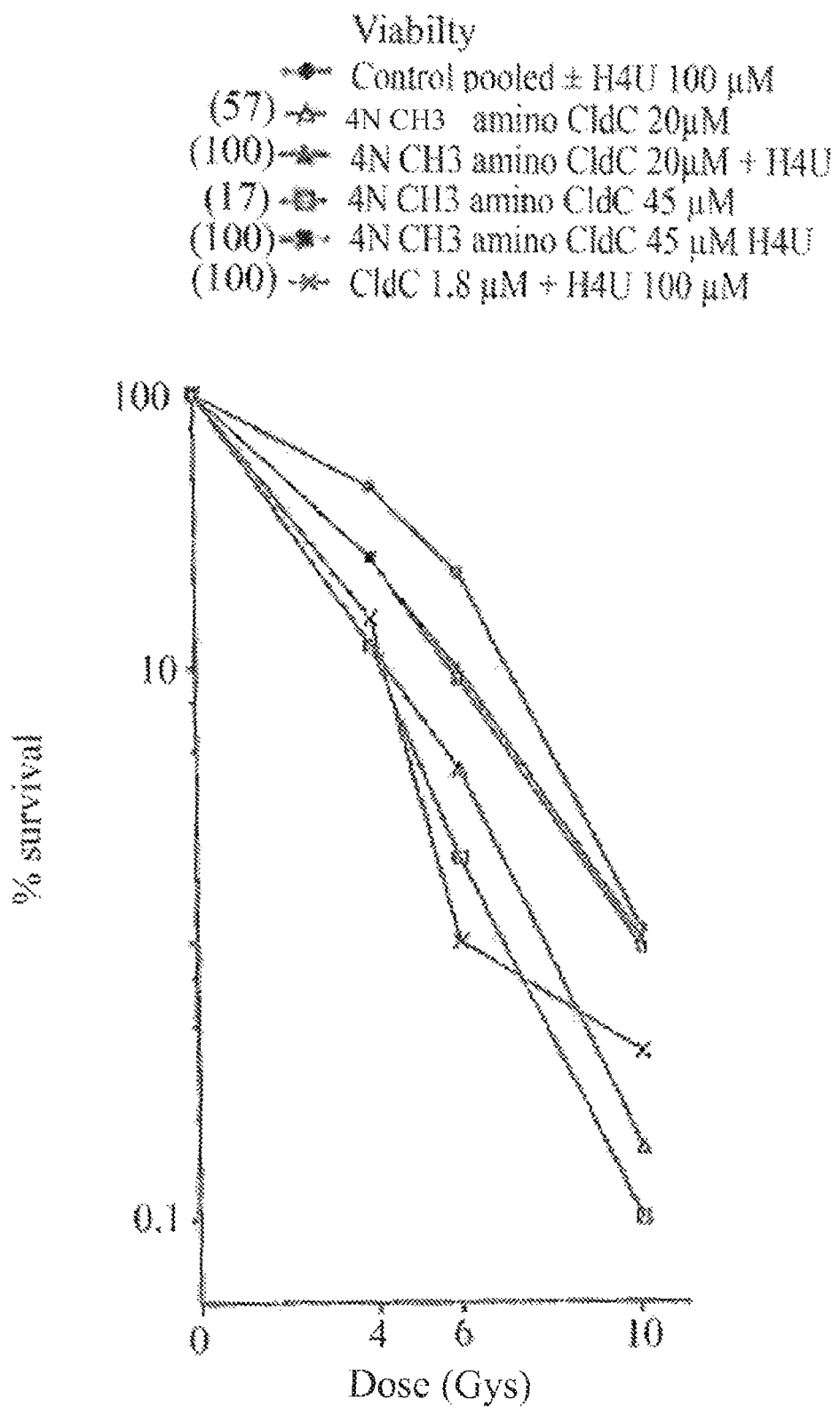
Figure 4:
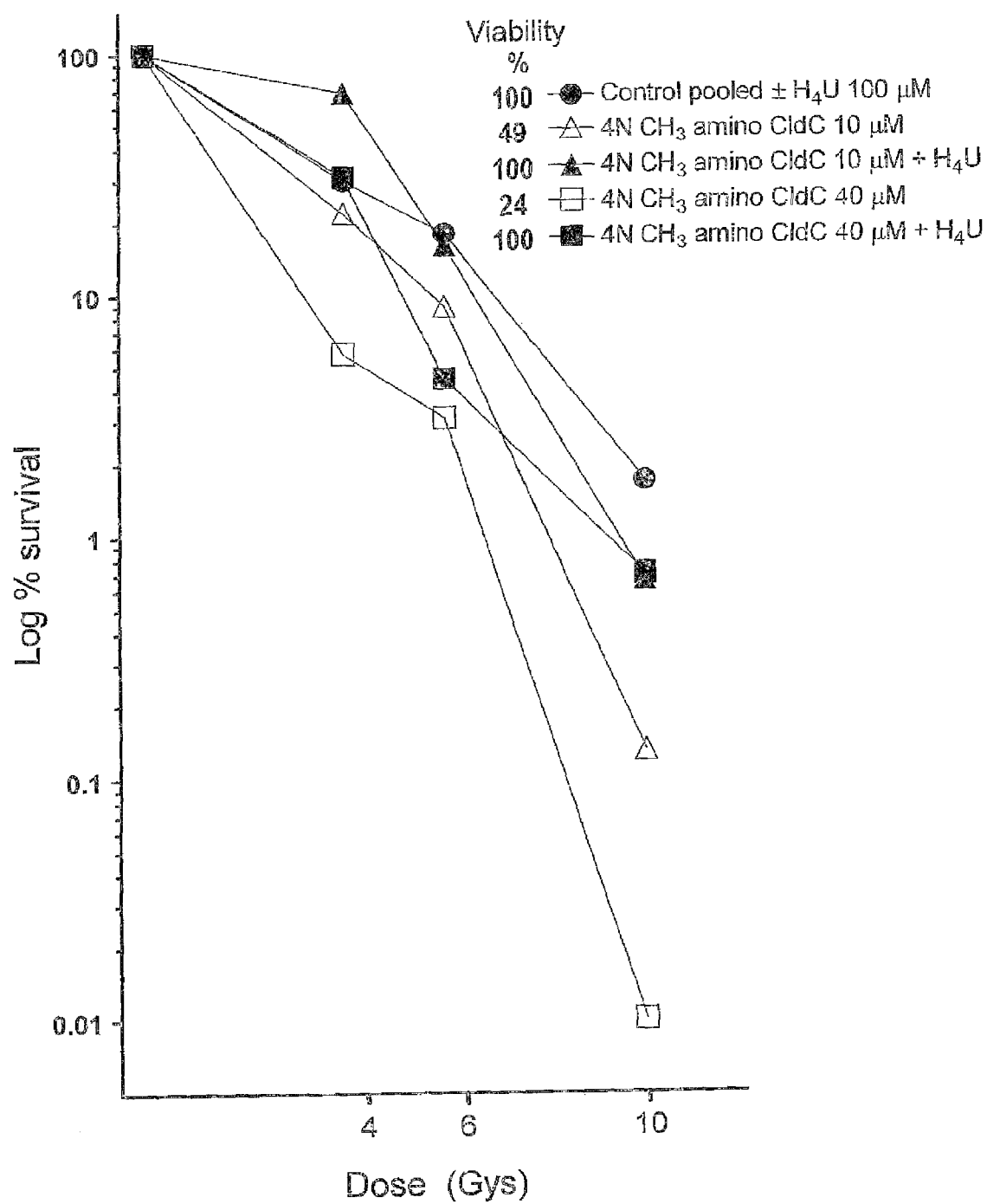

This drug has been shown to be a radiosensitizer of a prostatic tumor cell line; furthermore, its toxicity and radiosensitization are antagonized by tetrahydrouridine (H4U), an inhibitor of cytidine deaminase. See FIGS. 2 to 4.

Insight into the use of 4N, methylamino 5-halogenated-2'-deoxycytidine analogs first emerged when 4N, alkylamino 5-Iodo-2'-deoxycytidine analogs were synthesized as antiherpetic agents (Fox, L., Dobersen, M. J., and Greer, S. Incorporation of 5-Substituted Analogs of Deoxycytidine into DNA of Herpes Simplex Virus-Infected or -Transformed Cells Without Deamination to the Thymidine Analog. *Antimicrobial Agents and Chemotherapy* 23:465-476 (1983)). There was no indication from that study whether 4N, methylamino 5-Iodo-2'-deoxycytidine was a substrate for cellular deoxycytidine kinase or cytidine deaminase. The impetus for the study was the previous finding from the inventor's laboratory that 5-halo-2'-deoxycytidine analogs are substrates for the herpes encoded nucleoside kinase (Cooper, G. M. *Proc. Nail. Acad. Sci.* 70: 3788-3792; Schidkraut, S., Cooper, G. M., and Greer, S. *Mol. Pharm.* 11:153-158 (1975); Greer, S., Schildkraut, I., Zimmerman, T., and Kaufman, H. *Annals of the N.Y. Acad. of Sci.: Chemistry, Biology and Clinical Uses of Nucleoside Analogs* 255:359-365 (1975)). The finding that 4-N, methylamino5-CldC and 4-N, methylamino 5-FdC are not substrates for deoxycytidine kinase of human tumor cells is surprising and unanticipated.

It should be noted that a competition study suggests that the analogs which competes, binds competitively to the substrate binding site of cytidine deaminase and is, thus, a substrate. It is possible, but unlikely that the competitor merely binds but is not a substrate for cytidine deaminase.

The evidence that 4-N, methylamino 5-Chloro-2'-deoxycytidine is a substrate for cytidine deaminase is also indicated indirectly from the findings that it is toxic to cells in culture and it is a radiosensitizer and that these properties can be antagonized by Tetrahydrouridine, an inhibitor of cytidine deaminase. Thymidine antagonizes the radiosensitization of this drug which is consistent with the mechanism of its action shown in FIG. 1A.

5-Iodo-2'-deoxycytidine (IdC) and 5-Bromo-2'-deoxycytidine (IdC): These drugs has never been used in man with the strategy of exploring elevated levels of CD. 5-Iodo- and 5-Bromodeoxycytidine are very poor substrates for deoxycytidine kinase (Cooper, G. M., and Greer, S. *Mol. Pharm.* 9:704-710 (1973); Cooper, G. M., and Greer, S. *Mol. Pharm.* 9:698-703 (1973)) and Table C, but are good substrates for cytidine deaminase (Table D).

Figure 5:
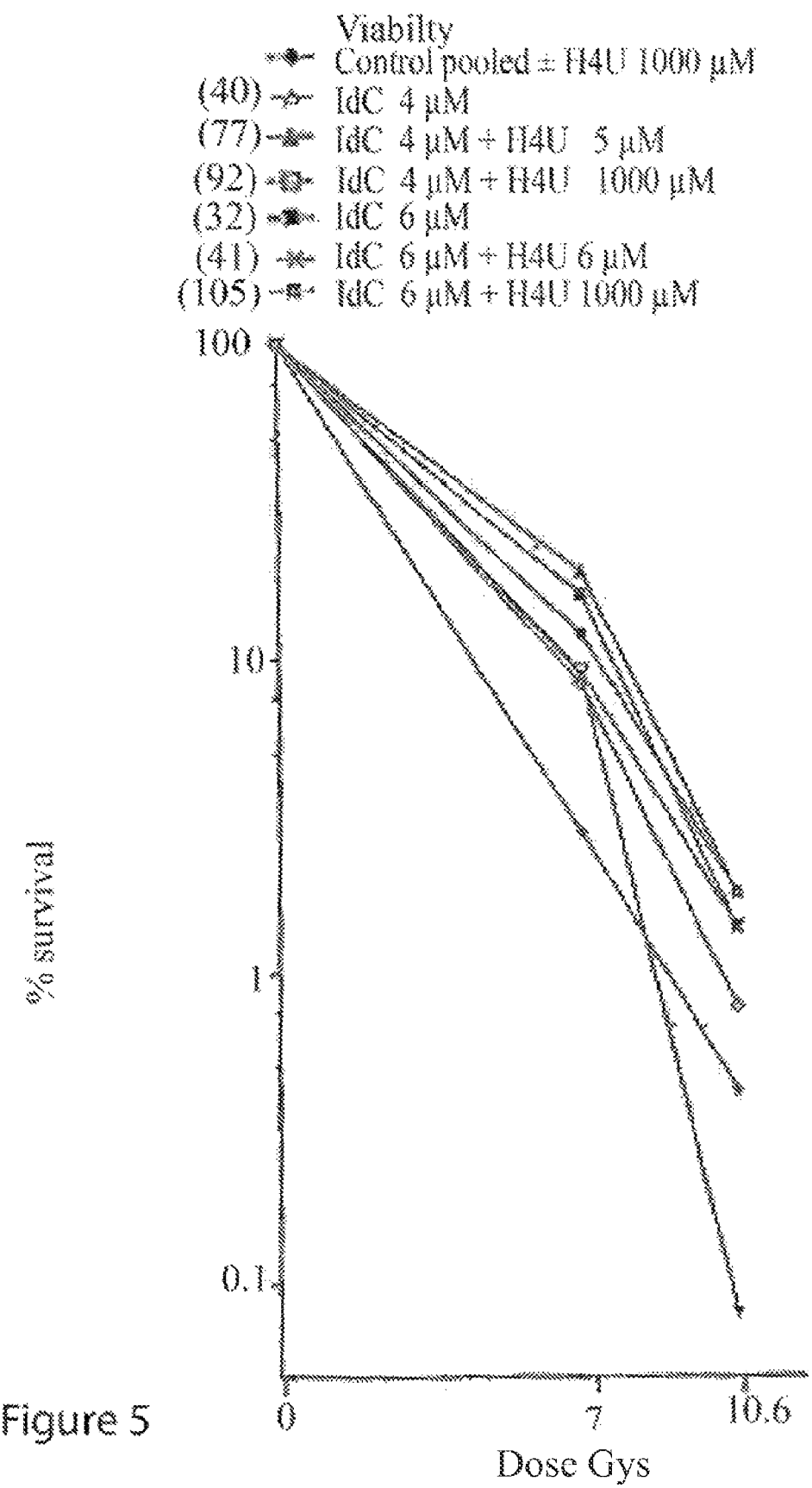
FIG. 5 is a graph showing the radiosensitization by 5-Iododeoxycytidine (IdC) and the reversal by $H_4U$ of Radiosensitization and cell killing. This indicates that the pathway of radiosensitization as well as cytotoxicity involves cytidine deaminase. Radiosensitization by 4-N, methylamino CldC, IdC and BrdC was antagonized by thymidine indicating that the target of these drugs is DNA as shown in FIGS. 1A, 1B and 1C. The cytotoxicity of 4N, methylFdC and 5-Trifluoromethyl deoxycytidine was also prevented by tetrahydrouridine and antagonized by thymidine consistent with the indicated metabolic pathway and indicated targets in FIGS. 1D and 1E.
Figure 5A:
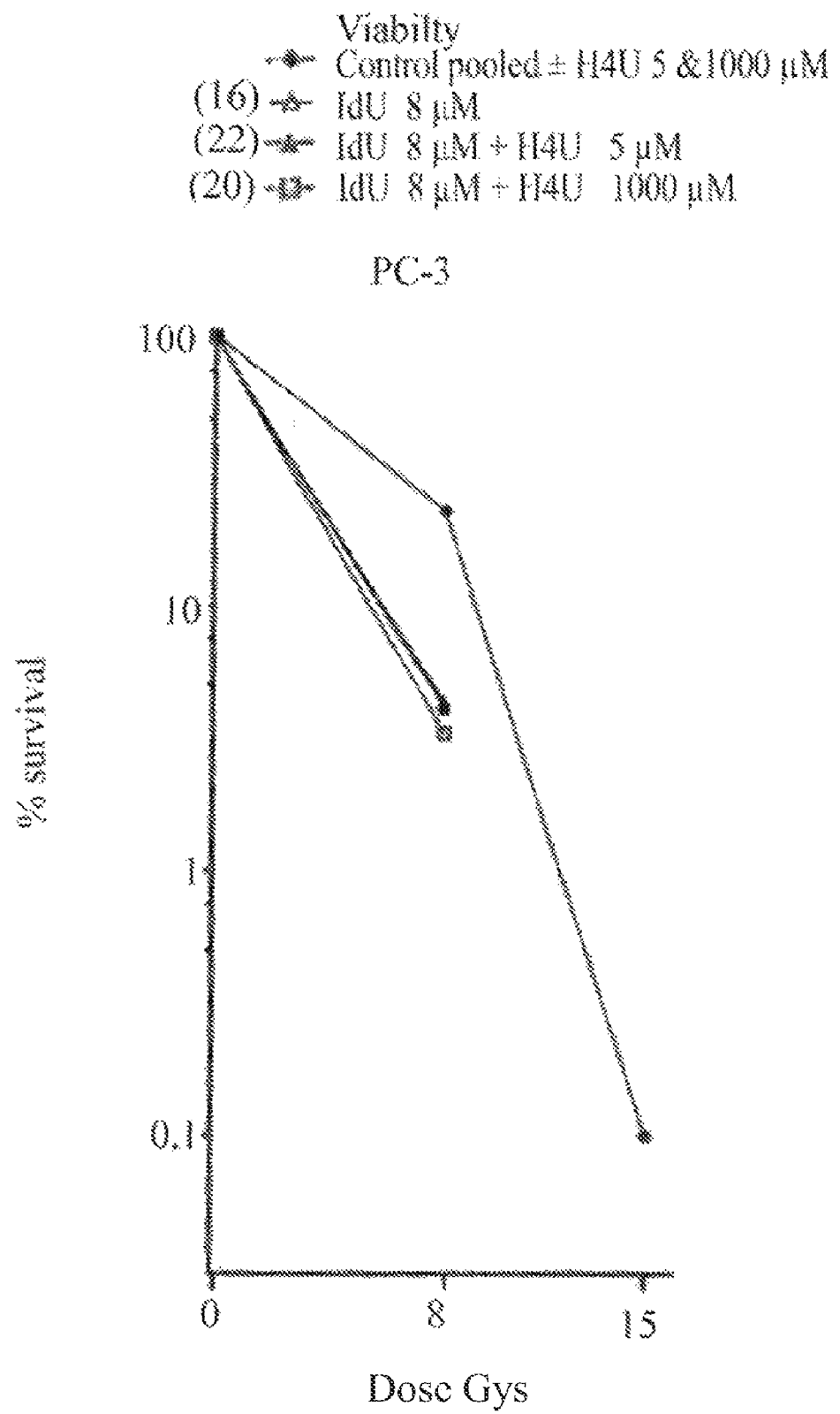
FIG. 5A is a graph showing the results obtained by radiosensitization by 5-Iododeoxyuridine. Also shown is the relative lack of the effect of tetrahydrouridine on the toxicity and radiosensitization of IdU (which lacks an amino group) in contrast to the effects seen in FIG. 5 and Table E with IdC.

Both drugs are effective radiosensitizers of cells in culture and as the case with 4-N, methylamino-5-CldC, the radiosensitization (FIG. 5), and toxicity (Table E) of IdC, for example, are antagonized by high doses of H4U, the inhibitor of cytidine deaminase. In a similar manner, the toxicity and radiosensitization are antagonized by thymidine.

Figure 1C:
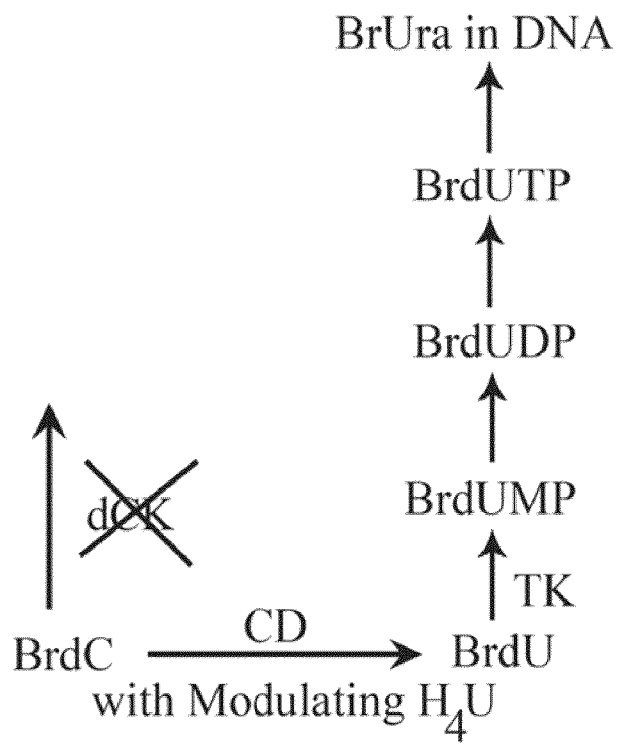

The fact that 5 μM H4U, when combined with IdC resulted in greater radiosensitization than IdC alone is likely due to the protection provided IdC from catabolism when it is converted to IdU. The pyrimidine nucleoside phosphorylases and, ultimately dihydrouracil dehydrogenase are the enzymes involved in the catabolic pathway. Tetrahydrouridine did not affect the radiosensitization of IdU in the manner it affected IdC. The pathway by which 5-Iododeoxycytidine and 5-Bromodeoxycytidine are converted to radiosensitizers is shown in FIGS. 1B and 1C.

Restoring Activity to Genes that are Silenced: The means by which these drugs could be effectively incorporated into DNA is shown in FIG. 1 and FIGS. 1A, B and C. Of interest is that the three halogenated analogs of deoxycytidine described as radiosensitizers are also capable of unsilencing genes that have been silenced (Fan, J., et al. Cancer Res. 65: 6927-6933 (2005)). This is another important mechanism of the anticancer activity of these drugs by converting these drugs to gene-unsilencing agents.

Novel Therapy—(Chemotherapy)

5-Trifluoromethyl-2'-deoxycytidine: This drug was custom synthesized as an antiherpetic agent (Barletta, J. and Greer, S. *Antiviral Research* 18:1-25 (1992)). This drug was examined as an antitumor agent against a rodent tumor (Mekras, J., Boothman, D., and Greer, S. *Cancer Research* 45:5270-5280 (1985)). However, its utilization against human pancreatic tumors as an inhibitor of thymidylate synthetase could not be predicted and was not evident until the enzymatic findings of elevated cytidine deaminase were obtained as described above.

Figure 1D:
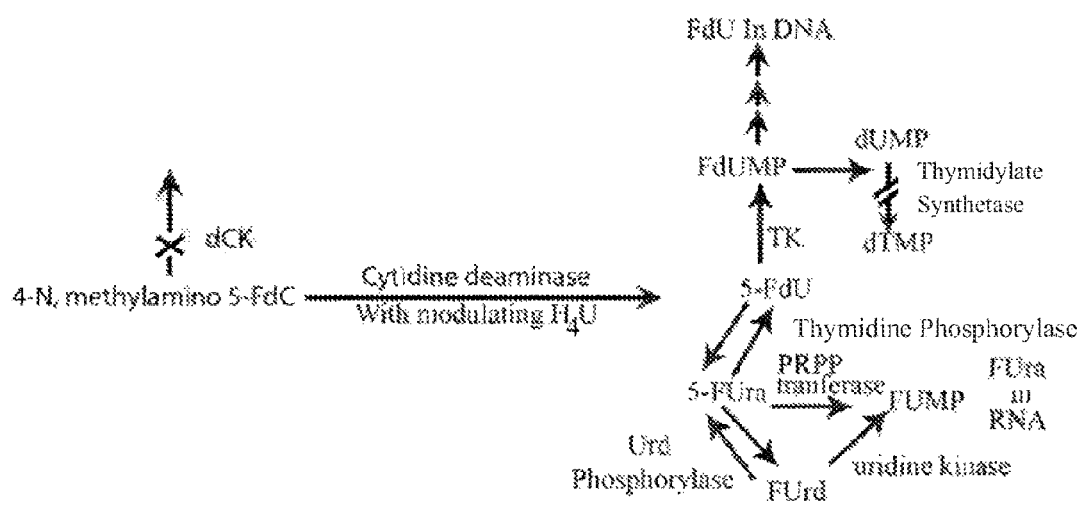
Figure 1E:
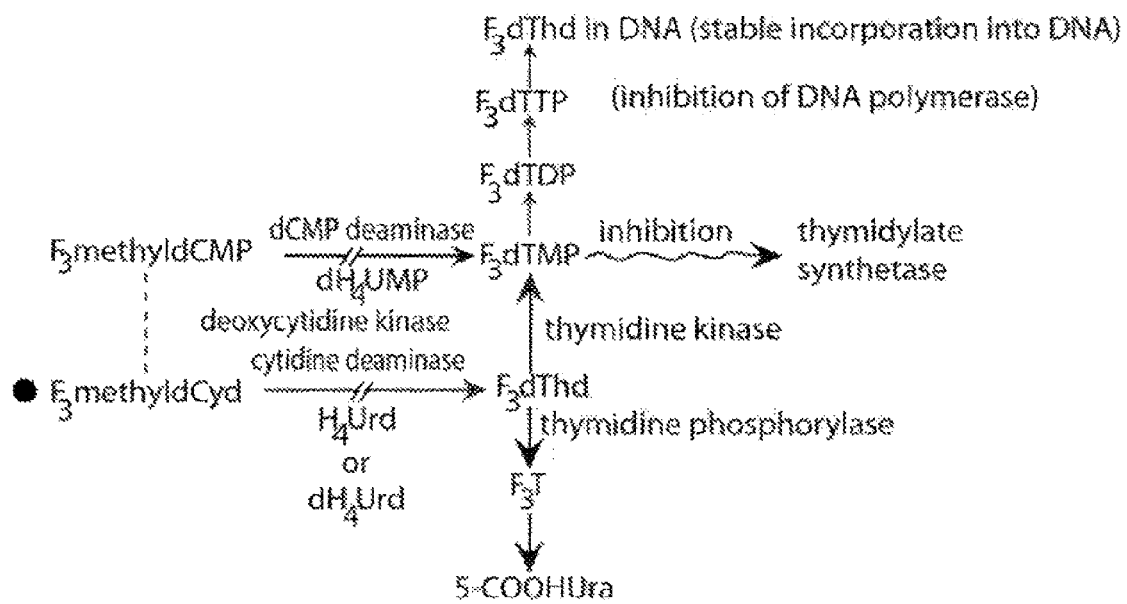

5-Trifluoromethyl-2'-deoxycytidine is a poor substrate for dCKas shown in table C, but is a reasonably good substrate for cytidine deaminase as shown in Table D. It is not a radiosensitizer, but will selectively be metabolized in the pancreatic tumor to inhibit its growth by inhibiting DNA synthesis in view of the fact that 5-trifluoromethyl thymidine will be converted by thymidine kinase to 5-trifluoromethyl TMP an inhibitor of thymidylate synthetase, a key target of chemotherapy. It will also inhibit tumor DNA polymerase. FIG. 1E shows the pathway of metabolism of $F_3$methyldC in Pancreatic Tumors where its metabolites will selectively inhibit thymidylate synthetase and DNA polymerase. Table E shows that the inhibition of growth of PC-3 cells in culture by 5-trifluoromethyldC can be antagonized by H4U, the inhibitor of cytidine deaminase. This is consistent with the pathway of metabolism of 5-$F_3$methyldC shown in FIG. 1E.

All five drugs can be coadministered with a modulating dose of Tetrahydrouridine to prevent deamination by systemic (liver) cytidine deaminase.

All five drugs can also be utilized for other human tumors in which cytidine deaminase levels are elevated including tumors of the lung, colon/rectum, breast, head and neck, uterus, cervix, colon, liver esophagus and others.

An unanticipated strategy is now available vs. brain tumors possessing high levels of cytidine deaminase as it was found that deoxycytidine and its analogs cross the blood-brain barrier (Spector R. and Huntoon S. *J. Neurochem.* 41:1131-1136 (1983)).

4-N, methylamino-5-Fluoro-2'-deoxycytidine: This drug was custom synthesized by the inventor as a drug that would be activated by deoxycytidine kinase and serve as a hypomethylating agent. Unexpectedly, it was found not to be a substrate for deoxycytidine kinase, but is a moderate to poor substrate for cytidine deaminase. The pathway of its metabolism is shown in FIGS. 1 and 1D.

This means that Pancreatic tumors and other tumors with elevated levels of cytidine deaminase will be able to generate the following antimetabolites: a) FdUMP, an inhibitor of thymidylate synthetase, b) FUMP, an inhibitor of mRNA maturation and RNA synthesis, FdUTP, which will be incorporated into DNA resulting in the formation of single strand breaks due to the action of uracil N-glycolyase which will remove 5-fluorouracil from DNA as well as uracil in DNA which is incorporated due to the accumulation of dUMP, the substrate of thymidylate synthetase. The removal of 5-Fluorouracil and uracil from DNA is then followed by the action of apurinic/apyrimidinic endonuclease which result in DNA strand breakage—largely but not completely followed by short patch repair by the sequential actions of an exonuclease, DNA polymerase and DNA ligase. The total of all these effects contribute to tumor growth inhibition and tumor kill.

The inhibition of thymidylate synthetase by $F_3$dTMP described in above will also result in accumulation of uracil in DNA as the substrate of the inhibited reaction dUMP is converted to dUDP→dUTP→uracil in DNA.

Figure 6:
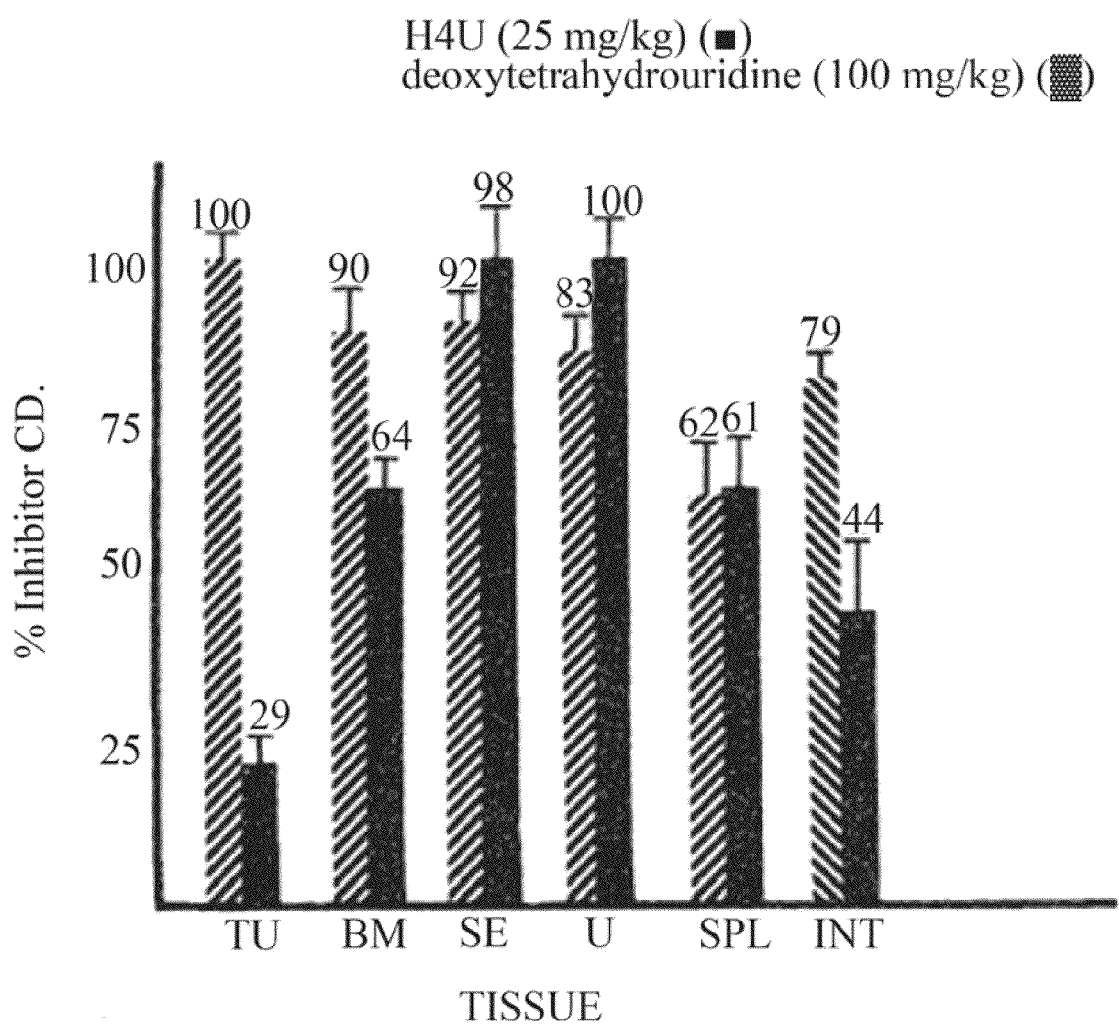
FIG. 6 is a graph showing the extent of inhibition of tumor (TU), bone marrow (BM), serum (SE), liver (LI), spleen (SPL), and intestinal (INT), cytidine deaminase (CD) levels following the i.p. administration of $H_4U$ (25 mg/kg) (■) or deoxytetrahydrouridine (100 mg/kg) (■) in 60 min. The extent of inhibition of the cytidine deaminase of the mouse mammary adenocarcinoma-755 compared to inhibition of the cytidine deaminase of normal tissues by H4U is shown. A comparison with the effects of deoxytetrahydrouridine is also shown. Only Tetrahydrouridine inhibited tumor CD to a much lower extent than the CD of normal tissues.

Selective inhibition of the cytidine deaminase of normal tissue by Tetrahydrouridine: Tetrahydrouridine (25 mg/kg) given to BD2F1 mice bearing Lewis Lung Carcinoma displayed the following % inhibition 60 minutes after IP injection: tumor, 8.6; liver, 100; spleen, 98; intestine, 93; bone marrow, 95; kidney, 96; skeletal muscle, 100; serum 100 (Table F). Similar results were obtained a separate study with Lewis lung carcinoma in BD2 F1 mice in which it was shown that 10 mg/kg of H4U did not confer the Selectivity that 25 and 50 mg/kg conferred and 75 mg/kg was too high a dose because inhibition of CD in the tumor increased from 33% at 25 and 50 mg/kg to 93%. The efficacy of the drug, $F_3$methyldC followed the pattern of Selectivity. The mean day of death (Tumor/Control) was 1.3, 1.6, 1.8 and 1.4 for 10, 25, 50 and 75 mg/kg H4U, respectively. These results are shown in Table G. Similar results were obtained with the mouse mammary adenocarcinoma-755 in BD2F1 mice with only 29% inhibition of tumor but with 100, 61, 44, 90 and 95% inhibition of the cytidine deaminase in liver, spleen, intestine, bone marrow and serum, respectively, as shown in FIG. 6.

If tumor cells possess a CD that is relatively refractory to inhibition by modulating doses of Tetrahydrouridine (or other CD inhibitors in category II) this is not in conflict with the proposal that high doses of these inhibitors, when used by themselves, may have antitumor effects. Tetrahydrouridine, which has been used in man, is nontoxic and is an effective CD inhibitor. Deoxytetrahydrouridine did not display a selective inhibition of normal tissue cytidine deaminase. Furthermore, dCMP deaminase of normal tissue was not selectively inhibited by H4U or dH4U.

Uridine/Kinase:

In view of the marked elevation of cytidine deaminase, which resulted a therapeutic approach with 5 novel drugs which are 5 halogenated pyrimidine analogs, we observed that another enzyme of pyrimidine metabolism, uridine/cytidine kinase, though low in the majority of pancreatic tumors (elevated ≥2-fold in only 33% of pancreatic tumors and ≥4-fold on only 10% of pancreatic tumors as shown in Table H), this enzyme (U/C kinase) was found to be substantially elevated ≥2-fold in tumors of the lung, colon/rectum, breast and brain. Elevations over that of normal adjacent tissue ≥4-fold is characteristic of a substantial percent of these tumors as can be seen in Table H.

Two novel 5-halogenated analogs which would be activated (phosphorylated) by this enzyme were synthesized and studied to determine if they were substrates of uridine/cytidine kinase and if the chlorinated ribonucleoside analogs were radiosensitizers. The radiosensitizers are the ribosides, 5-chloruridine and 5-chlorocytidine.

In addition, 5-fluorocytidine could serve as a chemotherapeutic and hypomethylating agent for patients with tumors with high levels of this activating enzyme, uridine/cytidine kinase. 5-fluorouridine is a drug that is currently seldom used for treating patients; however, in this invention of enzyme driven selective target directed radio- and chemotherapy, there may be a new use for this abandoned agent.

Figure 7:
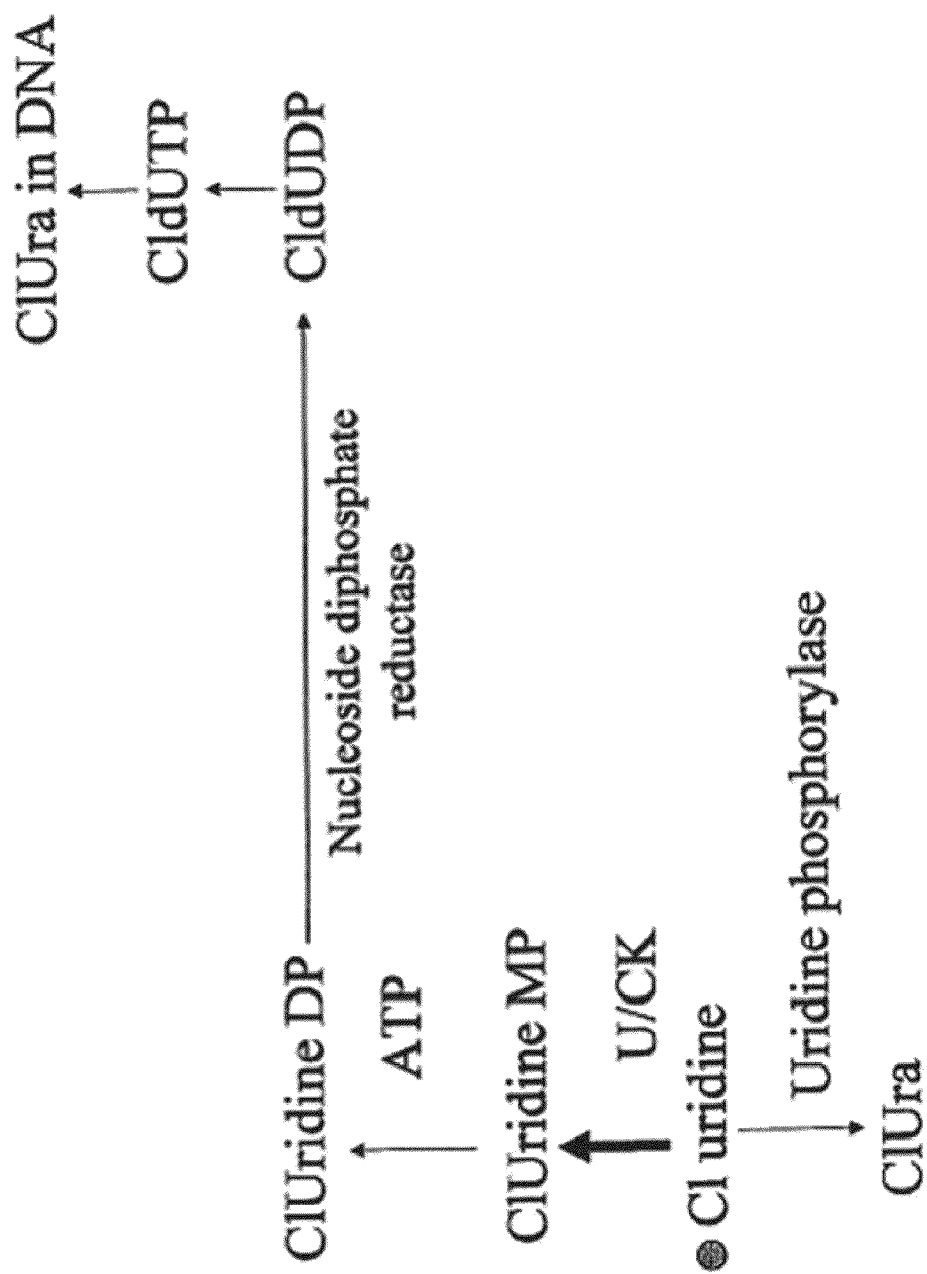
FIG. 7 is a schematic representation showing the pathway the pathway of metabolism of 5-Chlorouridine to Radiosensitize tumors via activation by uridine/cytidine kinase. 5-chlorocytidine would be effective vs. tumors with high levels of both U/C kinase and cytidine deaminase and could be given with or without a cytidine deaminase inhibitor.

FIG. 7 shows the pathway of metabolism of 5-chlorouridine as a radiosensitizer of tumor cells with elevated U/C kinase. 5-chlorocytidine would be effective vs. tumors with high levels of both U/C kinase and cytidine deaminase and could be given with or without a cytidine deaminase inhibitor.

Table J show that 5-Chlorouridine and 5-Chlorocytidine are moderate substrates for the U/C kinase of T24 cells (a human bladder tumor cell line). The fluorinated analogs are better substrates.

Figure 8:
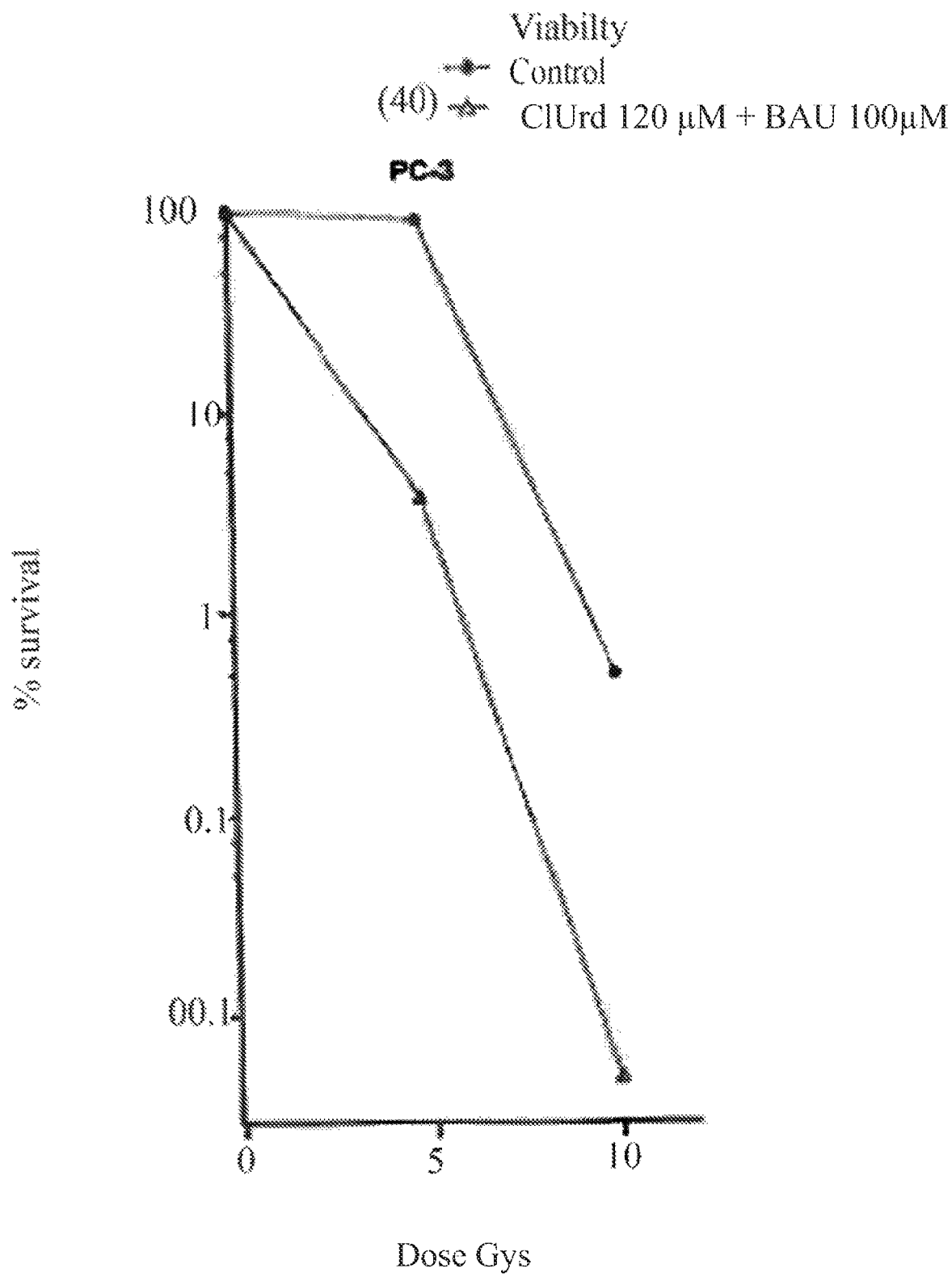
FIG. 8 is a graph showing radiosensitization of PC-3 cells by 5-Chlorouridine, the riboside. 5-Benzylacyclouridine was added to inhibit uridine phosphorylase.
Figure 9:
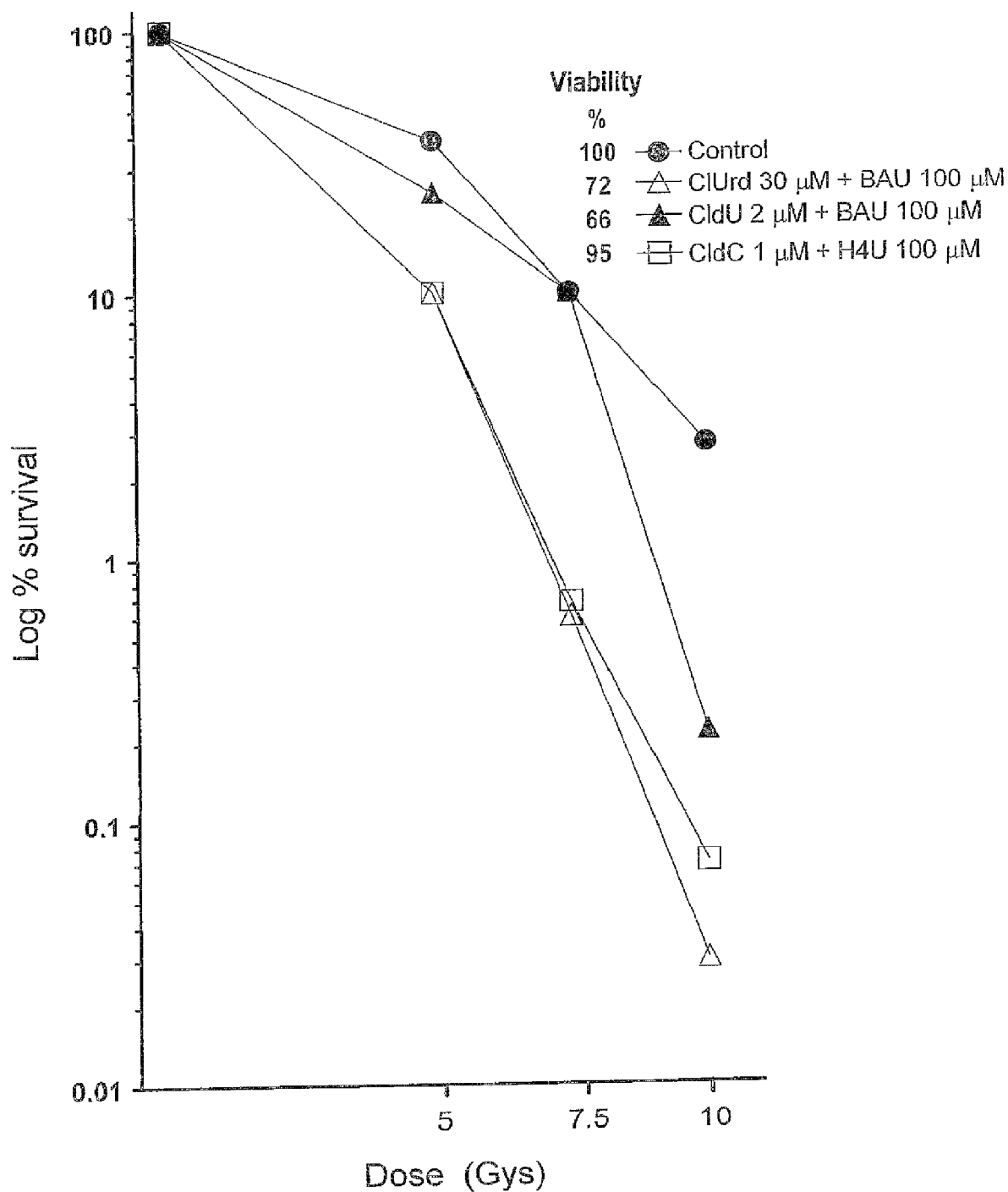
FIG. 9 is a graph showing radiosensitization of PC-3 cells by 5-Chlorouridine. Comparison with 5-Chlorodeoxyuridine (CldU) and 5-Chlorodeoxycytidine plus $H_4U$ in modulating doses. 5-Benzacyclouridine was added in all studies in which the effects of a uridine or deoxyuridine analog was examined to inhibit uridine phosphorylase.
Figure 10:
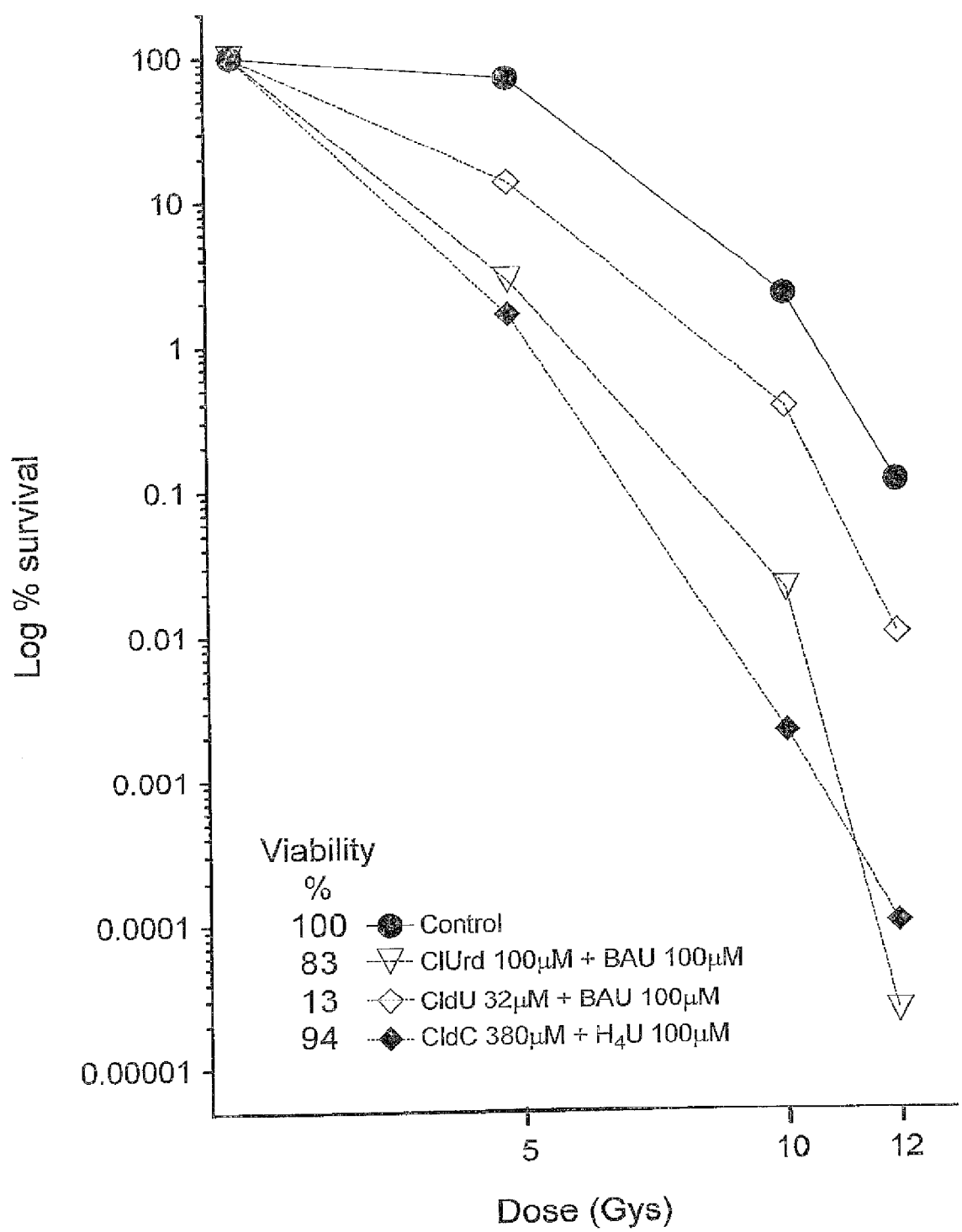
FIG. 10 is a graph showing radiosensitization by 5-Chlorouridine in T24 cells (a human bladder cancer cell line). Comparison with CldU and CldC plus $H_4U$ is shown.
Figure 11:
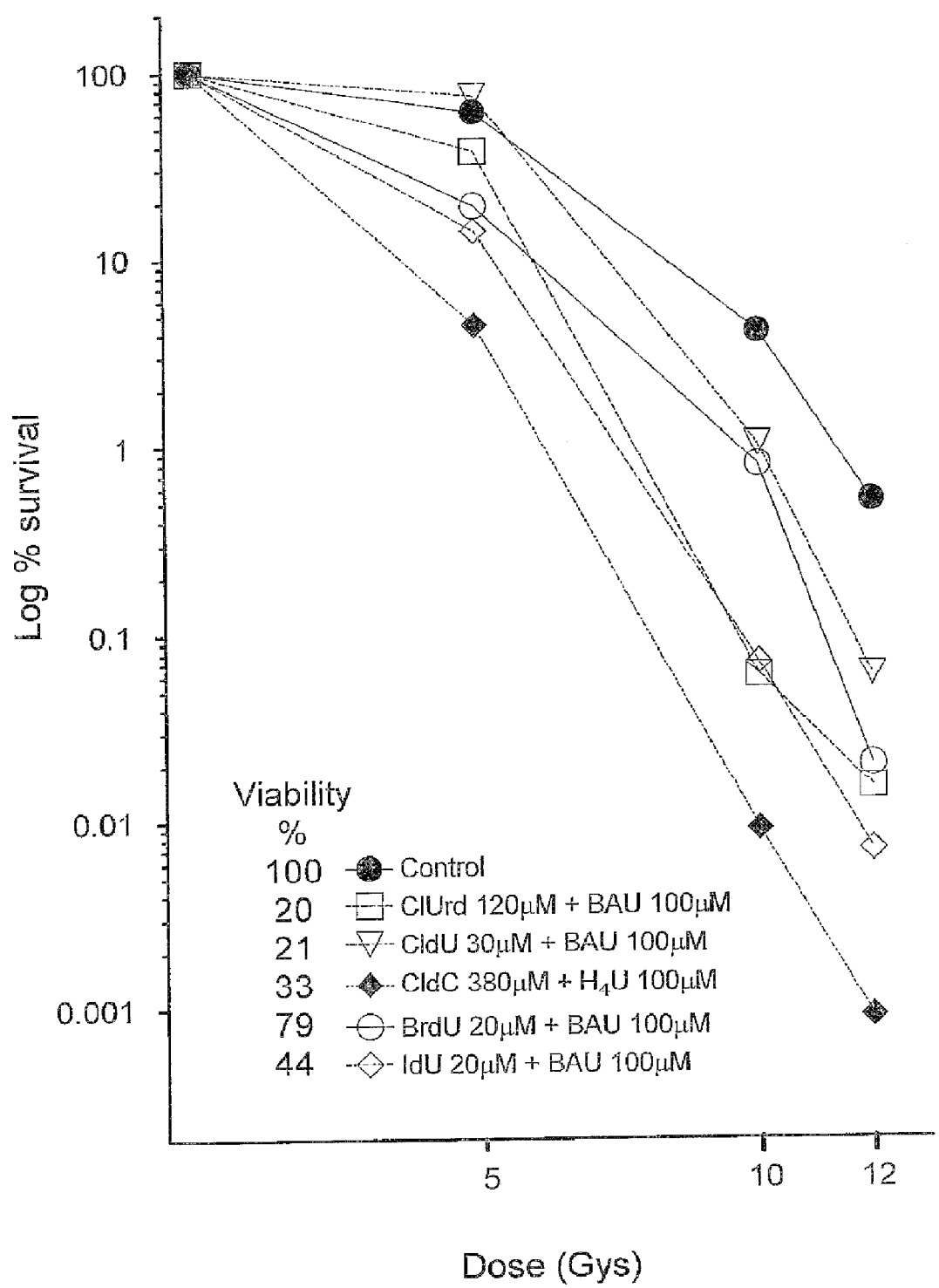
FIG. 11 is a graph showing radiosensitization by 5-Chlorouridine in T24 cells. A comparison with CldU, BrdU, IdU and CldC plus $H_4U$ is shown. Chlorouridine compared very favorably with the other established Radiosensitizers.

FIGS. 8 and 9 with PC3 cells demonstrate that 5-Chlorouridine is an effective radiosensitizer at doses with which very little cell killing occurred in the absence of radiation. This can also be seen in FIGS. 10 and 11 with T24 cells. Benzacyclouridine (BAU) was added to inhibit uridine phosphorylase.

In FIG. 12 radiosensitization with 5-Chlorocytidine can be seen. Unexpectedly H4U decreases viability of the PC-3 cells exposed to ClCyd and decreases radiosensitization by this analog. The decrease in viability may be an effect due to incorporation into RNA.

TABLE F

Effect of 25 mg $H_4$U/kg mouse weight upon cytidine deaminase of Lewis lung carcinoma and various normal tissues, 60 minutes after i.p. administration

| Tissue | Cytidine deaminase[b] | % of inhibition[c] |
|---|---|---|
| Tumor, LLC | 2,330 ± 76.6[a] | 8.61 ± 1.16 |
| Liver | 12.1 ± 1.42 | 100 ± 1.00 |
| Spleen | 84.8 ± 8.16 | 97.6 ± 2.40 |
| Intestine | 139 ± 0.25 | 93.3 ± 0.68 |
| Bone marrow | 507 ± 0.70 | 95.2 ± 0.50 |
| Serum | 76.8 ± 1.48 | 100 ± 0.20 |
| Kidney | 136 ± 8.94 | 95.8 ± 1.05 |
| Skeletal muscle | 1.83 ± 0.01 | 100 ± 0.40 |

[a]$H_4$U, 25 mg/kg, was injected i.p. into animals bearing bilaterally implanted s.c Lewis lung carcinoma with tumor volumes of 1500-3000 mm³. Tissues were excised and assayed for the various enzyme activities assording to the protocols described previously and in "Materials and Methods".
[b]Levels represent control enzyme activities using [³H]dCyd as substrate from untreated animals. Enzyme activity was defined as nmol/g protein/15 min.
[c]Calculated by dividing $H_4$U-treated enzyme activities and then multiplying the ratio by 100%. Inhibition values measured as "0.0" indicate neither inhibition nor significant activation.

TABLE G

Effect of administration of $H_4$U on cytidine deaminase and dCMP deaminase activity of tumor, serum and other tissues assayed 30 min after $H_4$U addition % of inhibition of deaminating enzyme activity assayed 30 min after addition of $H_4$U

| $H_4$Urd (mg/kg) | MDD[a] T/C | Cytidine deaminase | | | | | | dCMP deaminase of tumor |
|---|---|---|---|---|---|---|---|---|
| | | Serum | Spleen | Liver | Bone marrow | Intestine | Tumor[b] | |
| 10 | 1.25 | 45 | 0 | 0[c] | | | 18 | 0[d] |
| 25 | 1.63 ± 0.07[e] | 100 | 100 | 100 | 62 | 52 | 33 ± 2.0 | 0 |

TABLE G-continued

Effect of administration of H$_4$U on cytidine deaminase and dCMP deaminase activity of tumor, serum and other tissues assayed 30 min after H$_4$U addition
% of inhibition of deaminating enzyme activity assayed 30 min after addition of H$_4$U

|  |  | Cytidine deaminase | | | | | | dCMP |
|---|---|---|---|---|---|---|---|---|
| H$_4$Urd (mg/kg) | MDD[a] T/C | Serum | Spleen | Liver | Bone marrow | Intestine | Tumor[b] | deaminase of tumor |
| 50 | 1.78 ± 0.06 | 100 | 93 | 90 | 66 | 57 | 33 ± 1.0 | 0 |
| 75 | 1.44 | 98 | 84 | 98 | 84 | 65 | 93 ± 7.0 | 0 |

[a]MDD, mean day of death.
[b]Ten-day-old Lewis lung carcinoma; 1500 to 3000 mm$^3$.
[c]Less than 3% enzyme inhibition.
[d]Less than 5% enzyme inhibition.
[e]Mean ± SE.

TABLE H

The Effectiveness of 5-Chlorouridine and 5-Chlorocytidine to act as substrates for uridine/cytidine kinase in competition with the phosphorylation of uridine; a comparison with other relevant nucleosides and their analogs in crude extracts of the cell line, T$_{24}$.

| Nucleoside Competitor | μM | Ratio: Competitor Substrate Substrate: $^3$H-Uridine* (16.7 μM) | % Inhibition |
|---|---|---|---|
| 5-Chlorouridine | 750 | 50 | 32 |
|  | 500 | 30 | 24 |
|  | 250 | 15 | 22 |
|  | 100 | 6 | 11 |
| Uridine | 750 | 50 | 90 |
|  | 500 | 30 | 87 |
|  | 250 | 15 | 80 |
|  | 100 | 6 | 62 |
| 5-Chlorocytidine[‡] | 250 | 15 | 23 |
|  | 100 | 6 | 2 |
| Cytidine | 750 | 45 | 96 |
|  | 500 | 30 | 90 |
|  | 250 | 15 | 89 |
|  | 100 | 6 | 57 |
| 5-Fluorouridine | 250 | 15 | 80 |
|  | 100 | 6 | 56 |
| 5-Fluorocytidine | 250 | 16 | 58 |
|  | 100 | 6 | 34 |
| Deoxyuridine | 250 | 15 | 0** |
| Deoxycytidine | 250 | 15 | 0 |
| 5-Chlorodeoxyuridine | 250 | 15 | 0 |
| 5-Chlorodeoxycytidine | 250 | 15 | 0 |
| Tetrahydrouridine | 1500 | 90 | 1.7 |
| 5-Benzacyclouridine | 1500 | 90 | 7.0 |

*5-Benzacyclouridine was added throughout to inhibit uridine phosphorylase
[‡]Tetrahydrouridine was added to substrates which are cytidine or deoxycytidine or their analogs
0** Values were equal (or slightly greater) than values obtained with no competitor (baseline).

Protein concentration: 0.3-0.38 mg/ml in several repetitive experiments in which results were pooled.

TABLE J

The Effectiveness of 5-Chlorouridine and 5-Chlorocytidine to act as substrates for uridine/cytidine kinase in competition with the phosphorylation of cytidine; a comparison with other relevant nucleosides and their analogs in crude extracts of the cell line, T$_{24}$.

| Nucleoside Competitor | μM | Ratio: Competitor Substrate Substrate $^3$H-Cytidine* (8.3 μM) | % Inhibition |
|---|---|---|---|
| 5-Chlorouridine[‡] | 750 | 90 | 39 |
|  | 500 | 60 | 32 |
|  | 250 | 30 | 21 |
|  | 100 | 12 | 8 |
| Uridine | 750 | 90 | 86 |
|  | 500 | 60 | 80 |
|  | 250 | 30 | 75 |
|  | 100 | 12 | 59 |
| Chlorocytidine | 500 | 60 | — |
|  | 250 | 30 | 24 |
|  | 100 | 12 | 10 |
| Cytidine | 500 | 60 | 88 |
|  | 250 | 30 | 85 |
|  | 100 | 12 | 66 |
| 5-Fluorouridine | 250 | 30 | — |
|  | 100 | 12 | — |
| 5-Fluorocytidine | 500 | 60 | 66 |
|  | 250 | 30 | 51 |
|  | 100 | 12 | — |
| Deoxyuridine | 250 | 30 | — |
| Deoxycytidine | 500 | 60 | 20 |
|  | 250 | 30 | 10 |
| 5-Chlorodeoxyuridine | 200 | 30 | 7.0 |
| 5-Chlorodeoxycytidine | 500 | 60 | 5.1 |
|  | 250 | 20 |  |
| 5-Fluorodeoxycytidine | 500 | 30 | 4.8 |
| Tetrahydrouridine | 1500 | 180 | 1.5 |
| 5-Benzacyclouridine | 1500 | 180 | 0 |

*Tetrahydrouridine was added throughout to inhibit cytidine deaminase
[‡]5-Benzacyclouridine was added to uridine and its analogs to inhibit uridine phosphorylase
0** Values were equal (or slightly greater) than values obtained with no competitor (baseline).

Protein concentration: 0.36-0.4 mg/ml in several repetitive experiments in which results were pooled.

What is claimed is:

1. A method of treating a tumor cell comprising administering a composition comprising a radiosensitizing agent, in a therapeutically effective concentration, comprising:
   4-N, methylamino-5-chloro-2'-deoxycytidine with a cytidine deaminase inhibitor combined with or without one or more sources of radiation and treating a tumor cell.

2. The method of claim 1, wherein the tumor is characterized by elevated levels of cytidine deaminase as compared to levels of cytidine deaminase in a normal cell.

3. The method of claim 1, wherein the sources of radiation comprise X-rays, γ-rays, protons, brachytherapy, yttrium-90, β-rays, π-mesons, monoclonal antibodies attached to Radionuclides, stereotactic radio surgery, 3-Dimensional Conformal Radiation and Intensity Modified Radiation Therapy.

4. The method of claim 1, wherein the cytidine deaminase inhibitor comprises tetrahydrouridine, or tetrahydro-2'-deoxyuridine.

5. The method of claim 1, wherein the composition is administered to a tumor cell in an amount effective to prevent, minimize, or reverse the development or growth of a tumor cell.

6. A radiosensitizing composition comprising 4-N, methylamino-5-chloro-2'-deoxycytidine and a cytidine deaminase inhibitor.

7. A method of treating a cancer patient comprising: administering to a patient a composition comprising a radiosensitizing agent, in a therapeutically effective concentration, comprising:
   4-N, methylamino-5-chloro-2'-deoxycytidine with a cytidine deaminase inhibitor combined with or without one or more sources of radiation and treating a cancer patient.

8. The method of claim 7, wherein the cancer is characterized by elevated levels of cytidine deaminase as compared to levels of cytidine deaminase in a normal individual.

9. The method of claim 7, wherein the sources of radiation comprise X-rays, γ-rays, protons, brachytherapy, yttrium-90, β-rays, π-mesons, monoclonal antibodies attached to Radionuclides, stereotactic radio surgery, 3-Dimensional Conformal Radiation and Intensity Modified Radiation Therapy.

10. The method of claim 7, wherein the cytidine deaminase inhibitor comprises tetrahydrouridine, tetrahydro-2'-deoxyuridine.

11. The method of claim 7, wherein the composition is administered to a patient in an amount effective to prevent, minimize, or reverse the development or growth of a tumor in the patient upon administration to the patient.

12. The method of claim 7, wherein the composition is delivered to a patient by slow intratumoral release, intra-muscularly, intra-venously, orally or nasally.

13. The method of claim 7, wherein the chemotherapeutic agent or cytidine deaminase inhibitor is administered in an amount of about 1 mg/kg/individual to 50 mg/kg/individual.

14. The method of claim 7, wherein the chemotherapeutic agent is deaminated and unsilences genes in a tumor cell which restore normal cell functions.

15. A method of treating a tumor comprising administering to a patient a composition comprising 4-N, methylamino-5-Cl-2'-deoxycytidine, with a modulating cytidine deaminase inhibitor and with or without radiation therapy.

16. A method of treating a pancreatic tumor cell comprising administering a composition comprising 4-N, methylamino 5-fluoro-2'-deoxycytidine with a cytidine deaminase inhibitor.

17. The method of claim 15, wherein the tumor is a brain tumor, a pancreatic tumor or a colorectal tumor.

18. The method of claim 1, wherein the tumor cell is a pancreatic tumor cell.

19. The radiosensitizing composition of claim 6, wherein 4-N, methylamino-5-chloro-2'-deoxycytidine and a cytidine deaminase inhibitor are in amounts effective for inhibiting growth of a pancreatic tumor.

20. The method of claim 7, wherein the cancer patient has a pancreatic tumor.

21. The method of claim 15, wherein the tumor is a pancreatic tumor.

* * * * *